US011590189B2

(12) United States Patent
Fança-Berthon et al.

(10) Patent No.: US 11,590,189 B2
(45) Date of Patent: Feb. 28, 2023

(54) THERAPEUTIC USE OF A FRAXIMUS AUGUSTIFOLIA EXTRACT

(71) Applicant: NATUREX S.A., Avignon (FR)

(72) Inventors: Pascale Elizabeth Renée Fança-Berthon, Le Thor (FR); Leila Denise Falcao, Avignon (FR); Antoine Charles Bily, Vedene (FR); Marc Roller, Morieres les Avignon (FR); Simona Birtic, Cavaillon (FR)

(73) Assignee: Naturex S.A., Avignon (FR)

( * ) Notice: Subject to any disclaimer, the term of this patent is extended or adjusted under 35 U.S.C. 154(b) by 947 days.

(21) Appl. No.: 16/320,257

(22) PCT Filed: Jul. 25, 2017

(86) PCT No.: PCT/EP2017/068788
§ 371 (c)(1),
(2) Date: Jan. 24, 2019

(87) PCT Pub. No.: WO2018/019844
PCT Pub. Date: Feb. 1, 2018

(65) Prior Publication Data
US 2019/0269745 A1 Sep. 5, 2019

(30) Foreign Application Priority Data
Jul. 25, 2016 (GB) ..................... 1612858

(51) Int. Cl.
A61K 36/63 (2006.01)
A23L 33/105 (2016.01)
A61P 1/16 (2006.01)
A61P 3/04 (2006.01)
A61K 9/00 (2006.01)
A61K 31/351 (2006.01)

(52) U.S. Cl.
CPC ............ A61K 36/63 (2013.01); A23L 33/105 (2016.08); A61K 9/0053 (2013.01); A61K 31/351 (2013.01); A61P 1/16 (2018.01); A61P 3/04 (2018.01); A23V 2002/00 (2013.01); A23V 2200/32 (2013.01); A23V 2200/328 (2013.01)

(58) Field of Classification Search
None
See application file for complete search history.

(56) References Cited

U.S. PATENT DOCUMENTS 8,293,292 B2  10/2012  He et al.

FOREIGN PATENT DOCUMENTS

CN   101918080 A   12/2010
JP   2011503009 A   1/2011
WO  2009061849 A1   5/2009

OTHER PUBLICATIONS

Garcia-Villalba, et al., Molecules, 20:22202. (Year: 2015).*
Ibarra, et al., Phytomedicine, 18:479. (Year: 2011).*
Willing, et al., Gastroenterology, 139:1844. (Year: 2010).*
Natal Gaspar, et al. Ethnobotany in the Center of Portugal (Santarem), ResearchGate, Jan. 2002.
Great Britain Search Report for Application No. 1612858.9 dated Apr. 20, 2017.
Francisco Gomez-Garcia, et al., Preventative Effect of a Fraxinus Excelsior L Seeds/Fruits Extract on Hepatic Steatosis in OBses Type 2 Diabetic Mice, Diabetes & Metabolism, Mar. 21, 2015, vol. 6, Issue 4.
I. Kostova, et al., Chemical components of Fraxinus species, Fitoerapia, pp. 85-106, Nov. 14, 2006, vol. 78, Issue 2, Elsevier.
International Search Report dated Aug. 30, 2017 in International Application No. PCT/EP2017/068788.
Written Opinion dated Aug. 30, 2017 in International Application No. PCT/EP2017/068788.
International Preliminary Report on Patentability dated Jan. 29, 2019 in International Application No. PCT/EP2017/068788.
Wiernsperger N. et al., Diabetes Metab. Syndr. Obes., 6, 379-388, (2013).
Younossi Z., et al., Clin. Gastroenterol Hepatol., 9, 524-530, (2011).
Carding S., et al., Microb. Ecol. Health Dis., 26, 26191, (2015).
Serino M., et al., Curr. Cardiol. Rep., 16(11), 540 (2014).
Boursier J. and Diehl, A. M., et al., PLoS Pathog, 11(1), e1004559 (2015).
Arslan N. et al., World J. Gastroenterol., 20(44), 16452-16463, (2014).
Fowler S. D., Greenspan P. et al., O. J. Histochem. Cytochem., 33, 833-836, (1985).
Takahashi Y., Soejima Y., Fukasato T., et al., World J. Gastroenterol., 18(19), 2300-2308, (2012).
Zhou Y. and Xie L., Am. J. Digest. Dis., 2(1), 60-67, (2015).
Kleiner D. E. and Brunt E. M., Semin. Liver Dis., 32, 3-13, (2012).
Louzpone C., Lladser M. E., Knights D., Stombaugh J., Knight R., (2011), UniFrac: an effective distance metric for microbial community comparison. ISME J. 5(2): 169-172.
Segata N., et al., Genome Biol., 12(6), R(60), (2011).
Touw, W. G. et al., Brief Bioinform., 14(3), 315-326, (2013).
Moulaoui Kenza et al., Eur. J. Med. Chem., 89, 179-188, (2014).
Meriem Berboucha et al., J. Med. Food, 13(4), 896-904, (2010).
Medjahed Zineb, et al., Turk. J. Med. Sci., 46(3), 910-920, (2016).
Milagros Rico, et al., J. Appl. Bot. Food Qual., 217-220, (2013).
Atmani, D., et al., Food Chem., 112(2), 303-309, (2009).
Visen, P., et al., J. Ethnopharmcol., 126(2), 226-232, (2009).
Lamaison, J. L., Plantes Medicinales et Phytotherapie, 25(1), 17-22, (1991).

* cited by examiner

Primary Examiner — Michael Barker
(74) Attorney, Agent, or Firm — Curatolo, Sidoti & Trillis Co., LPA; Salvatore A. Sidoti; Brittany L. Kulwicki

(57) ABSTRACT

The present invention relates to extracts from Fraxinus angustifolia samara, processes for providing such extracts, and methods and uses of the extracts obtained. In particular, the present invention relates to the use of such extracts in reversing obesity-related and/or metabolic syndrome-related gut microbiota dysbiosis treatment, treating or preventing hepatic steatosis, non-alcoholic fatty liver disease (NAFLD) and non-alcoholic steatohepatitis (NASH), and modulating and/or adjusting gut microbiota.

13 Claims, 14 Drawing Sheets

Figure 3
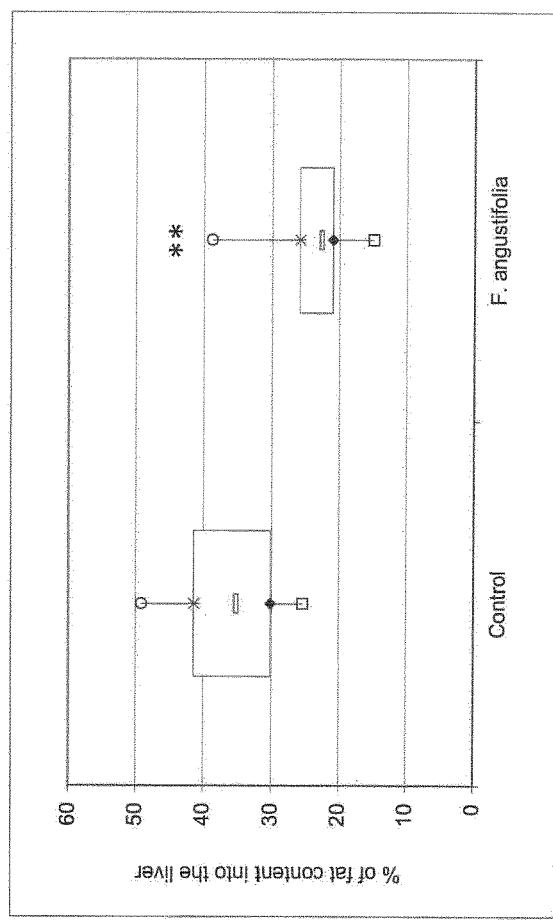
(B)
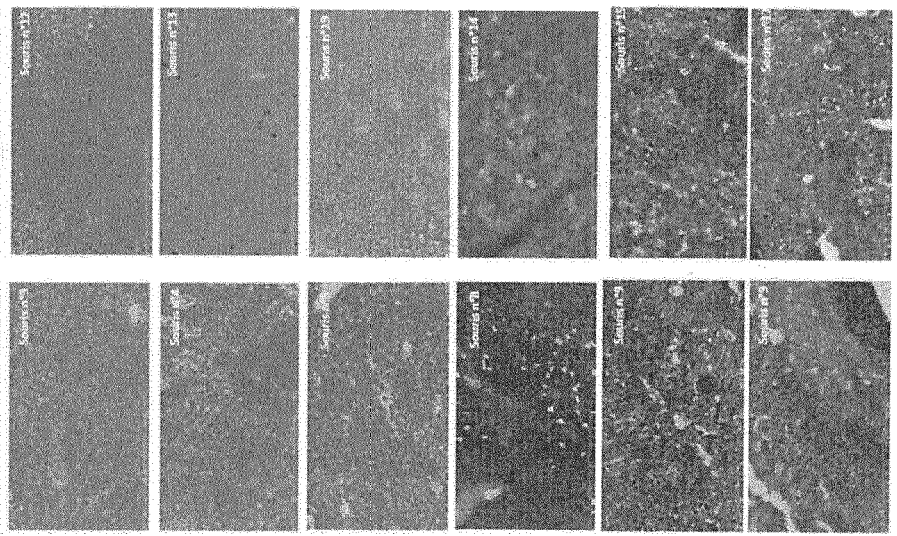
(A)

Figure 12
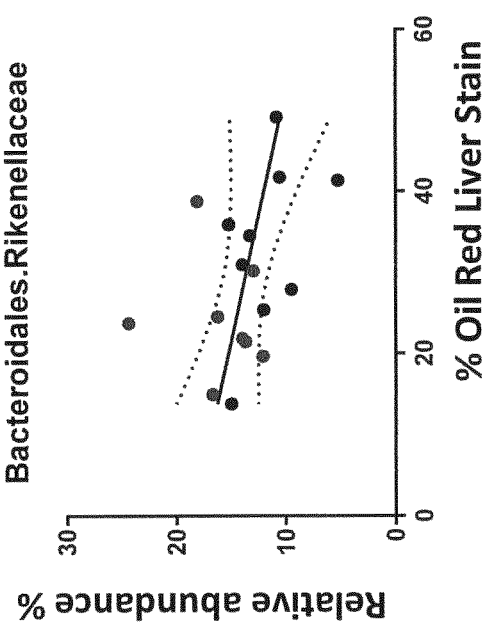
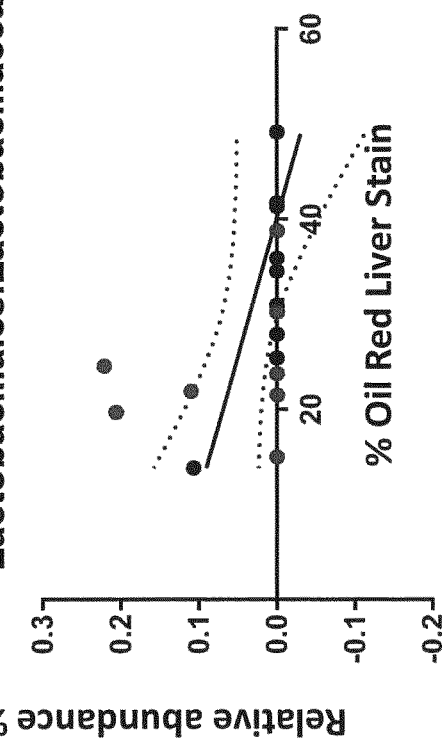
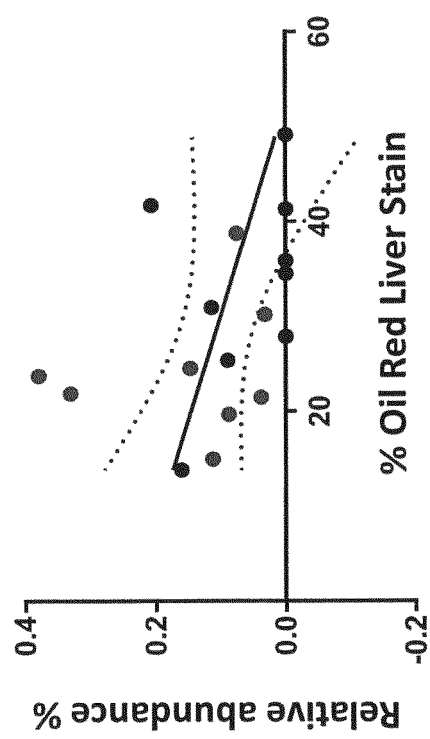
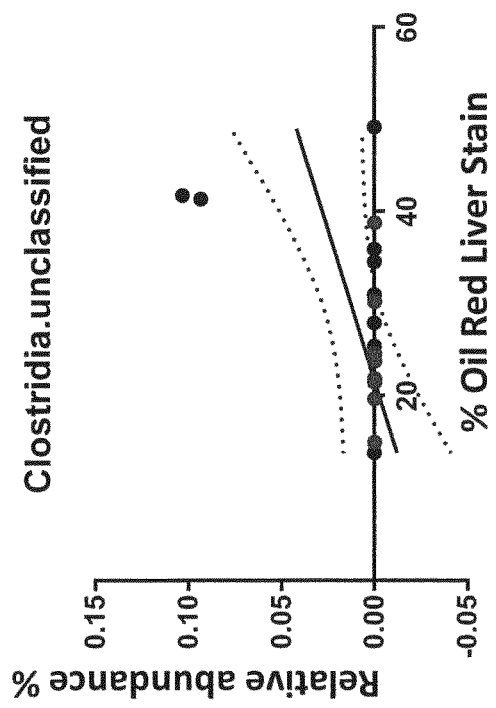

THERAPEUTIC USE OF A FRAXIMUS AUGUSTIFOLIA EXTRACT

This application is a U.S. National Stage Application of PCT/EP2017/068788, filed Jul. 25, 2017, which claims priority to Great Britain Patent Application No. 1612858.9, filed Jul. 25, 2016, both of which applications are incorporated by reference in their entireties.

The present invention relates to extracts from *Fraxinus angustifolia* (in particular, from the samara thereof), processes for providing such an extract, and methods and uses relating to such extracts. In particular, the present invention relates to methods of reversing obesity-related and/or metabolic syndrome-related gut microbiota dysbiosis treatment, treating or preventing conditions such as hepatic steatosis, non-alcoholic fatty liver disease (NAFLD) and non-alcoholic steatohepatitis (NASH), and modulating and/or adjusting gut microbiota.

The listing or discussion of an apparently prior-published document in this specification should not necessarily be taken as an acknowledgement that the document is part of the state of the art or is common general knowledge.

Non-alcoholic fatty liver disease (NAFLD) is a condition defined by excessive fat accumulation in the form of triglycerides (steatosis) in the liver (designated as an accumulation of greater than 5% of hepatocytes histologically). It is the most common liver disorder in developed countries; for example, affecting around 30% of US adults. If left undertreated, the condition may progressively worsen and may ultimately lead to cirrhosis of the liver. NAFLD is particularly prevalent in obese patents, with around 80% thought to have the disease.

A sub-group of NAFLD patients display liver cell injury and inflammation in addition to excessive fat accumulation. This condition, designated as non-alcoholic steatohepatitis (NASH), is virtually indistinguishable histologically from alcoholic steatohepatitis (ASH) (as described by the World Gastroenterological Organisation (WGO) in WGO Global Guidelines: Non-alcoholic Fatty Liver Disease and Non-alcoholic Steatohepatitis (2012)). While the simple steatosis seen in NAFLD does not directly correlate with increased short-term morbidity or mortality, progression of this condition to NASH dramatically increases the risks of cirrhosis, liver failure, and hepatocellular carcinoma (HCC).

While the morbidity and mortality from liver causes are greatly increased in patients with NASH, they correlate even more strongly with the morbidity and mortality from cardiovascular disease. NASH is widely considered to be the liver expression of the conditions generally referred to as metabolic syndrome, which include diseases related to diabetes mellitus type 2, insulin resistance, central (truncal) obesity, hyperlipidaemia, low high-density lipoprotein (HDL) cholesterol, hypertriglyceridemia, and hypertension (see, for example, Wiernsperger, N., *Diabetes Metab Syndr Obes*, 6, 379-388 (2013)).

There is at present a worldwide epidemic of diabetes and obesity. At least 1.46 billion adults were overweight or obese and, as of 2008, around 170 million of the world's children were designated as being overweight or obese. These numbers are continuing to rise, indicating that NASH will become an increasingly common liver problem in both rich and developing countries, increasing the global burden of liver disease and affecting public health and healthcare costs globally.

In 2012, it was estimated that NAFLD and NASH will increase five-year direct and indirect medical costs by around 26%. As indicated above, it is also now estimated that about 30% of all adults in developed countries have NAFLD, and it is thought that around 2-6% of such adults have NASH. In particular, NAFLD is thought to be affecting up to 70-80% of obese individuals (see, for example, Younossi, Z. M. et al., *Clin Gastroenterol Hepatol*, 9, 524-530 (2011)).

The exact cause of NASH has not been elucidated, and it is almost certainly not the same in every patient. It is most closely related to insulin resistance, obesity, and the metabolic syndrome; however, not all patients with these conditions have NAFLD/NASH, and not all patients with NAFLD/NASH suffer from one of these conditions. Nevertheless, given that NASH is a potentially fatal condition, leading to cirrhosis, liver failure, and HCC, an effective treatment is urgently required.

At the present time, there is no evidence-based approved drug therapy for NAFLD/NASH. Lifestyle change is critical in any attempt to reverse the course of NAFLD/NASH, and targets for therapy are insulin resistance and oxidative stress. Although several treatment options are being evaluated, the value of most treatments remains uncertain, or the effects reverse when they are discontinued. The goals of treatment for NASH are to reduce the histologic features, and improve insulin resistance and liver enzyme levels.

The human intestinal microbiota is made up of trillions of microorganisms, most of which are of bacterial and viral origin, that are considered to be non-pathogenic. The microbiota functions in tandem with the host's defences and the immune system to protect against pathogen colonisation and invasion. It also performs an essential metabolic function, acting as a source of essential nutrients and vitamins and aiding in the extraction of energy and nutrients, such as short-chain fatty acids (SCFA) and amino acids, from food (see, for example, Carding, S. et al, *Microb Ecol Health Dis*, 26, 26191 (2015)).

Microbial culture studies detect only a small number of the species of intestinal bacteria. Nowadays, composition and the diversity of intestinal microbiota is revealed by culture-independent genetic and metagenomic techniques. Metagenomic analysis and 16S ribosomal RNA gene sequencing have shown that at the phylum level, Firmicutes and Bacteriodetes dominate, with Actinobacteria, Proteobacteria, Fusobacteria, Spirochaetae, Verrucomicrobia and Lentisphaerae also being present (ibid.). While the dominating phyla are relatively constant between individuals, diversity increases along the taxonomic line, with each individual harbouring over a hundred unique species.

Gut microbiota has evolved with humans as a mutualistic partner; however, changes in the composition of the gut microbiota, i.e. alteration of the ecologic organization of the gut microbiota (commonly known as dysbiosis), have been found to be related to several clinical conditions, such as obesity, diabetes, atherosclerosis, allergic diseases, gastrointestinal diseases, autoimmune diseases and cancer (see, for example, Serino, M., et al., *Curr Cardiol Rep*, 16(11), 540 (2014)), and also to NAFLD (see, for example, Boursier, J. and Diehl, A. M., *PLoS Pathog*, 11(1), e1004559 (2015)). Indeed, it is thought that gut microbiota dysbiosis could lead to altered intestinal defence, increased bacterial translocation, in turn triggering tissue inflammation and hepatic steatosis.

The possible role of the intestinal microbiota in liver steatosis progression includes several potential mechanisms of action: induction of obesity by harvesting energy from otherwise indigestible dietary polysaccharides; regulation of gut permeability and stimulation of low grade inflammation; modulation of dietary choline metabolism; and stimulation of endogenous ethanol production by enteric bacteria (see Arslan, N., *World J Gastroenterol*, 20(44), 16452-16463 (2014)).

Moreover, it is thought that an obesogenic microbiota can alternate liver function by stimulating hepatic triglycerides and by modulating systemic lipid metabolism, which may indirectly impact the storage of fatty acids in the liver. Restoration of an optimal intestinal microbial system could therefore be a promising strategy for preventing steatosis progression and, in particular, arresting the progression of NAFLD to NASH.

The present inventors have now surprisingly found that extracts obtained from *Fraxinus angustifolia* (herein referred to as FA) samara or seed (particularly, from the samara) possess potent activity in reversing gut microbiota dysbiosis by modulating or adjusting gut microbiota. These effects suggest that such *Fraxinus angustifolia* extracts may have numerous therapeutic and non-therapeutic (e.g. cosmetic) uses, and uses in the prevention of medical conditions.

*Fraxinus angustifolia* Extracts

According to the present invention, there is provided a *Fraxinus angustifolia* (FA) extract (in particular, a *Fraxinus angustifolia* samara seed (particularly, samara) extract), which may be referred to hereinafter as the "extract of the invention".

Typically, the extract of the invention may be an extract obtained from FA (in particular, the samara or seed of FA) using processes as described herein.

For the avoidance of doubt, all references herein to a *Fraxinus angustifolia* (FA) extract will refer in particular to extracts obtained from FA samara or seed (more particularly, samara) extract. Moreover, as FA samara will contain FA seed, it will be understood that extracts from FA samara will comprise (or consist essentially/consist of) extracts from FA seeds (samara).

The extract of the invention may be an aqueous extract, an alcoholic extract or a hydro-alcoholic extract. Preferably, the extract of the invention is a hydro-alcoholic extract, such as a hydro-methanolic or hydro-ethanolic extract. For example, the extract of the invention may be a hydro-ethanolic extract obtained using an extraction solvent comprising from about 1 to about 99% ethanol in water, such as from about 30% to about 75% ethanol in water, or from about 30% to about 50% ethanol in water, such as from about 35% or from about 40% ethanol in water.

The term "aqueous extract" as used herein, refers to the extract obtained from *Fraxinus angustifolia* (FA) when the extraction from the plant (particularly, samara) has been performed using water as the only solvent.

The term "alcohol extract" as used herein, refers to the extract obtained from *Fraxinus angustifolia* (FA) when the extraction from the plant (particularly, samara) has been performed using alcohol as the only solvent. For example, 100% methanol and/or 100% ethanol.

The term "hydro-alcoholic extract' as used herein, refers to the extract obtained from *Fraxinus angustifolia* (FA) when the extraction from the plant has been performed using a mixture of water and alcohol. For example, from about 1% to about 99% alcohol (e.g. ethanol) in water, such an extract would be termed a hydro-ethanolic extract.

In certain embodiments, the extract of the invention may comprise (or consist essentially/consist of) the following compounds (secoiridoids):

(i) from about 1% to about 16% by weight of nuzhenide, such as from about 1% to about 15% by weight;

(ii) from about 1% to about 18% by weight of GL3, such as from about 1% to about 17% by weight;

(iii) from about 0.5% to about 1% by weight of oleoside methyl ester;

(iv) from about 0.03% to about 0.12% by weight of excelside B;

(v) from about 0.1% to about 1.7% by weight of GL5; and/or (e.g. and)

(vi) from about 0.08% to about 0.8% by weight of salidroside, such as from about 0.08% to about 0.7% by weight.

Unless otherwise stated herein, the weight percentages listed are based on the total weight of (dry) extract obtained.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

When we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% of the specified amount.

For example, in certain embodiments the extract of the invention may comprise (or consist essentially/consist of) about 10% by weight nuzhenide and/or (e.g. and) about 10% by weight GL3.

For the avoidance of doubt, the structures of the above-mentioned compounds are depicted below.

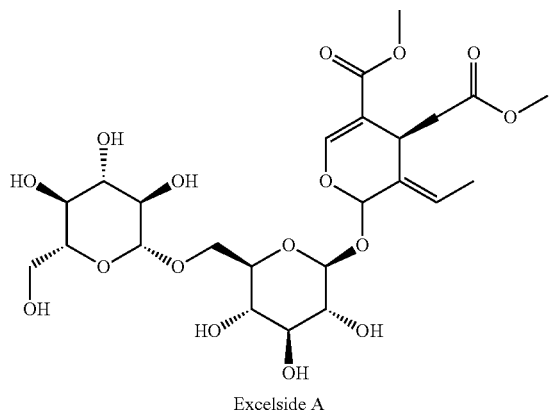

Excelside A

-continued
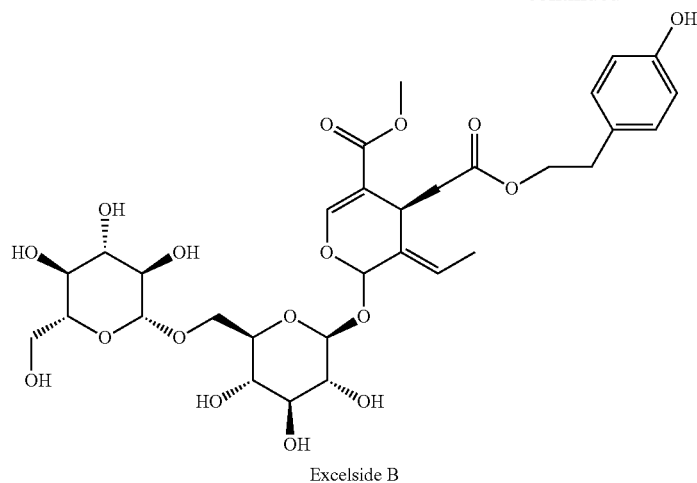
Excelside B
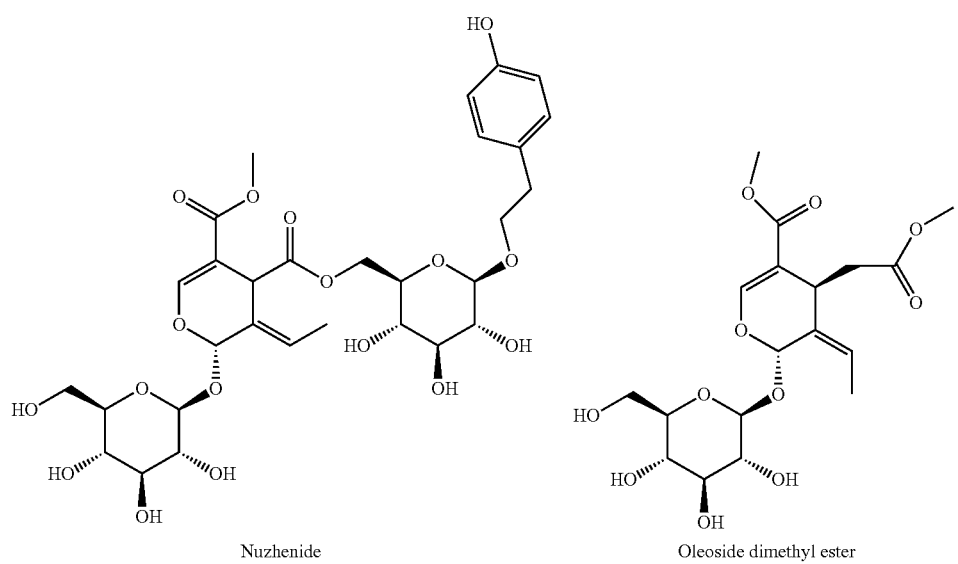
Nuzhenide
Oleoside dimethyl ester
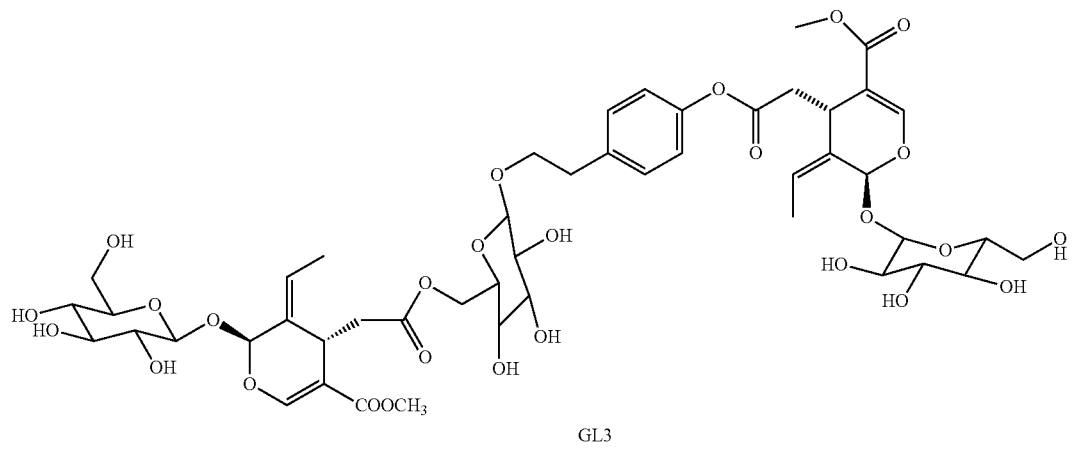
GL3

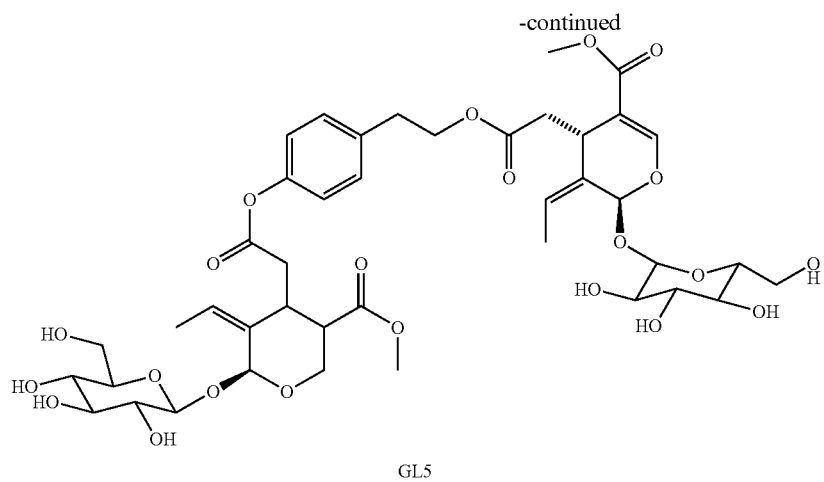

GL5

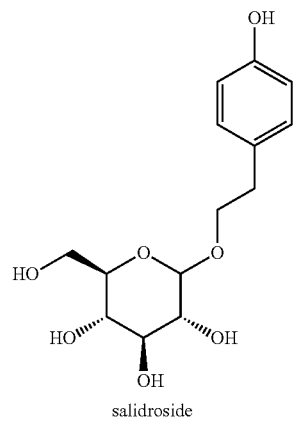

salidroside

Further, other compounds may also be present in the extract of the invention. In certain embodiments, other compounds that may be present include, but are not limited to, cumarins, such as fraxin, fraxetin, esculin, esculetin, scopolin, 7-methyl eculin and fraxidin glucoside.

For example, in certain embodiments, the extract of the invention may further comprise (or consist essentially/consist of):
fraxin (about 0.095%);
fraxetin (about 0.117%);
esculin (about 0.017%);
esculetin (about 0.017%);
scopolin (about 0.038%);
7-methyl eculin (about 0.040%); and/or (e.g. and)
fraxidin glucoside (about 0.061%).

In particular embodiments, total cumarins (estimated based on cumarins detected, as fraxin) were about 0.39%. Moreover, other cumarins may be identified (e.g. by LC/MS) at levels too low to be quantified (as their presence was below 5 ppm), but may include cichoriin, scopoletin, calyncantoside, mandshurin, fraxidin, isofraxidin and fraxinol.

The skilled person will understand that the extract of the invention may be provided in solid form. By solid form, it is included that the compound may be provided as an amorphous solid, or as a crystalline or part-crystalline solid.

Compositions and Administration

According to the present invention, the extract of the invention may be provided in the form of a (suitable) composition, such as a pharmaceutical composition or a food composition (which may be referred to as a functional food composition or a dietary composition).

In particular embodiments, the extract of the invention may be provided in the form of a pharmaceutical composition (which may also be referred to as a pharmaceutical formulation) or functional food composition comprising the extract of the invention and optionally a pharmaceutically acceptable excipient or (functional) food acceptable ingredient, as appropriate.

As used herein, references to pharmaceutically acceptable excipients may refer to pharmaceutically acceptable adjuvants, diluents and/or carriers as known to those skilled in the art.

Food acceptable ingredients include those known in the art (including those also referred to herein as pharmaceutically acceptable excipients) and that can be natural or non-natural, i.e. their structure may occur in nature or not. In certain instances, they can originate from natural compounds and be later modified (e.g. maltodextrin).

In particular embodiments, the extract of the invention may be provided in the form of a pharmaceutical composition or a functional food composition, further comprising a non-natural carrier or a modified natural carrier, such as maltodextrin.

By "pharmaceutically acceptable" we mean that the additional components of the composition are sterile and pyrogen free. Such components must be "acceptable" in the sense of being compatible with the extract of the invention and not deleterious to the recipients thereof. Thus, "pharmaceutically acceptable" includes any compound(s) used in forming a part of the formulation that is intended to act merely as an excipient, i.e. not intended to have biological activity itself. Thus, the pharmaceutically acceptable excipient is generally safe, non-toxic, and neither biologically nor otherwise undesirable.

The skilled person will understand that extracts of the invention (e.g. in the form of compositions, such as pharmaceutical compositions, as known to those skilled in the art, such as those as described herein) may be administered to a patient or subject (e.g. a human or animal patient or subject) by any suitable route, such as by the oral, rectal, nasal, pulmonary, buccal, sublingual, transdermal, intracisternal, intraperitoneal, and parenteral (including subcutaneous, intramuscular, intrathecal, intravenous and intradermal) route.

In particular, extracts of the invention may be administered orally. In such instances, pharmaceutical compositions according to the present invention may be specifically formulated for administration by the oral route.

Pharmaceutical compositions for oral administration include solid dosage forms such as hard or soft capsules, tablets, troches, dragees, pills, lozenges, powders and granules.

Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Compositions (e.g. pharmaceutical or food compositions) described herein, such as those intended for oral administration, may be prepared according to methods known to those skilled in the art, such as by bringing the components of the composition into admixture.

Such compositions as described herein may contain one or more additional components selected from the group consisting of food ingredients, such as sweetening agents, flavouring agents, colouring agents and preserving agents. Tablets may contain the active ingredient(s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Suitable pharmaceutical carriers include inert solid diluents or fillers, sterile aqueous solutions and various organic solvents. Examples of solid carriers are lactose, terra alba, sucrose, cyclodextrin, maltodextrin, talc, gelatine, agar, pectin, acacia, magnesium stearate, stearic acid, arabic gum, modified starch and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

Depending on the disorder, and the patient, to be treated, as well as the route of administration, extracts of the invention may be administered at varying doses (i.e. therapeutically effective doses, as administered to a patient in need thereof). In this regard, the skilled person will appreciate that the dose administered to a mammal, particularly a human, in the context of the present invention should be sufficient to affect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Typically, in the use or method of the invention described herein the extract or composition comprising the extract is administered in an amount of from about 100 mg/day to about 2000 mg/day, or from about 500 mg/day to about 1500 mg/day, or about 1000 mg/day.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

When included within a composition (e.g. a pharmaceutical composition) as described herein, the extract is typically present in an amount from about 1% by weight to about 100% by weight, for example, from about 10% by weight to about 90% by weight or about 20% by weight to about 80% or from about 30% by weight to about 70% or from about 40% by weight to about 60% by weight.

Processes for Obtaining Extracts

The extract of the invention may be isolated from FA seeds or samara (in particular, FA samara) using separation techniques that select for the required extract, which may be determined by those skilled in the art.

Typically, the extract of the invention may be obtained by the extraction and isolation processes as generally described herein below, or routine modifications thereof.

For example, processes for extraction and isolation of extracts of the invention may comprise (or consist essentially/consist of) the following steps:

(i) extraction of FA samara (which may be ground) by a suitable solvent;

(ii) evaporation of the solvent; and, if required (iii) purification of the extract (e.g. by chromatography).

Typically, FA samara are ground into granules with a particle size in a range from about 0.1 mm to about 30 mm, to increase the surface area for the solvent to contact and to increase extraction efficiency.

Particular solvents that may be used in the extraction process include alcohols such as methanol), and alcohol/water mixtures (such as mixtures of methanol and water). For example, the extraction solvents can be water, a water-alcohol mixture (from about 1% to about 99% alcohol in water. For example, from about 30% to about 75% alcohol in water, or from about 30% to about 50% alcohol in water, such as from about 35% or from about 40% alcohol in water), or alcohol. Particular alcohols that may be mentioned include ethanol (EtOH) and methanol (MeOH).

In particular embodiments, the extraction solvent may be an ethanol-water mix, such as from about 30% to about 75% ethanol in water, or from about 30% to about 50% ethanol in water. For example, from about 35% or from about 40% ethanol in water.

In one embodiment, the temperature of extraction is in a range of from about 20° C. to about 100° C. In a particular embodiment, the temperature for extraction is in a range of from about 50° C. to about 70° C.

Typically, the ratio of plant material to solvent mixture used in the extraction process varies from about 1:1 to about 1:10 on a gram to millilitre basis, such as from about 1:3 to about 1:8.

The incubation period (i.e. the period during which the plant material is in contact with the solvent) is typically from about 2 hours to about 24 hours.

After the plant materials and solvent have been incubated, the solvent is separated from residual plant material and the extraction composition is concentrated (i.e. the solvent is removed) until the extraction composition has a solid component. Typically, the solid component may comprise (or consist essentially/consist of) from about 1% to about 35% of FA secoiridoids. Other components include phenolic compounds, salidroside, coumarins and flavonoids.

After completion of the extraction process, the secoiridoid(s) can themselves be isolated from the FA extract (i.e. purified) used a chromatographic process, if required.

Typically, the extract of the invention may obtained using the following process:

the FA extract powder (i.e. obtained by preparing ground samara) is dissolved in an alcohol and the secoiridoid(s) are extracted by alcohol from the powder. The alcohol is then evaporated and the remaining residue including secoiridoid(s) is loaded into a chromatography column filled with reverse-phase C-18 resin;

several fractions containing different compounds are eluted with a series of water and 10% MeOH/90% water, and MeOH system. The fractions are compared by high performance liquid chromatography (HPLC) analysis and those elutes having similar HPLC patterns are combined;

the combined fractions are separated on normal phase silica gel column chromatography and eluted with chloroform ($CHCl_3$), $CHCl_3$-methanol mixture starting from 90%, 80% $CHCl_3$ to 100% MeOH to give several sub-fractions. The sub-fractions are compared by HPLC and the fractions which contain excelside A and excelside B are combined, respectively. The combined fractions are further purified by a combination of column chromatography over C-18, MCI GEL CHP-20P and/or Sephadex LH-20 resins to provide pure excelside A and excelside B.

The terms "isolated" and "purified" as used herein refer to the extract or secoiridoid(s) being separated from at least one other component (e.g. a polypeptide or cellulose derivative) present with the extract or secoiridoid(s) in its natural source. In one embodiment, the extract or secoiridoid(s) are provided in pure form or in the presence of a solvent, buffer, ion, or other component normally present in a solution of the same.

Thus, the terms "isolated" and "purified" do not refer to the extract or secoiridoid(s) present in their natural source. Similarly, the term extract refers to components of the natural material having been obtained through a process of extraction, rather than those components as present in their natural source (e.g. as FA seeds).

In particular embodiments, the extract of the invention as obtained from such processes may be:
substantially free of other plant material (e.g. free of plant cellulose);
substantially free of plant cells; and/or
substantially free of plant cellular matter.

As used herein, references to a material being "substantially free" of another material may refer to the material consisting of less than 1% by weight (e.g. less than 0.1%, such as less than 0.01% or less than 0.001%, by weight) of that other material.

In alternative embodiments, the method of extracting and isolating a FA extract from a FA seed may be described as comprising (or consisting essentially/consisting of) the steps of:
(a) grinding a FA seed into particles;
(b) containing the particles with a solvent mixture;
(c) separating the ground particles from the solvent mixture; and
(d) evaporating the solvent mixture.

In further such embodiments, the process may also comprise (or consist essentially/consist of) the steps of:
(e) dissolving the product of (d) in alcohol; and
(f) evaporating the alcohol.

Typically, in the extraction of the FA extract from an FA seed (i.e. steps (a) to (d) as described herein above): the ground particles have a diameter from about 0.1 mm to 30 mm; and/or the temperature is from about 20° C. to about 100° C.; and/or the ratio of ground particles to solvent mixture is from about 1 g to 1 ml to about 1 g to 8 ml; and/or the ground particles are in contact with the solvent mixture from about 2 hours to about 24 hours; and/or the solvent mixture is water, a water-alcohol mixture or alcohol.

In particular embodiments, the extract of the invention as described herein may be an extracted obtained from (or obtainable by) a process as described herein.

Therapeutic and Non-Therapeutic Uses

As described herein, the extract of the invention may have particular biological effects, which may be useful in the treatment of medical conditions. Thus, according to the present invention, there is provided the use of the extract of the invention in medicine (or as a pharmaceutical).

Further, as described herein, the extract of the invention may be particularly useful in the treatment of diseases, such as those described herein, such as hepatic steatosis (steatosis in the liver).

The extract of the invention may also assist patients in reducing or limiting weight gain. For example, the extract of the invention may reduce weight gain in a subject having a high fat diet (as shown in FIG. 1).

The extract of the invention may also reduce glucose intolerance. Typically, the extract of the invention may reduce glucose intolerance in a subject having a high fat diet (as shown in FIG. 2).

The extract of the invention may also reduce the level of fat deposited into the liver (hepatic steatosis). Typically, the extract of the invention may reduce the level of fat deposited into the liver in a subject having a high fat diet (as shown in FIG. 3).

Thus, in an aspect of the invention there is provided a *Fraxinus angustifolia* extract (i.e. an extract of the invention) for use in:
(a) reversing obesity-related and/or metabolic syndrome-related gut microbiota dysbiosis;
(b) treating or preventing hepatic steatosis, non-alcoholic fatty liver disease (NAFLD) and/or non-alcoholic steatohepatitis (NASH);
(c) treating or preventing leaky gut and/or intestinal hyperpermeability;
(d) treating or preventing gut microbiota dysbiosis-induced cardiovascular diseases and/or cardiometabolic diseases;
(e) treating or preventing low grade inflammation;
(f) treating or preventing atherosclerosis;
(g) treating or preventing obesity; and/or
(h) treating or preventing insulin resistance, glucose intolerance, prediabetes, and/or diabetes (such as type 2 diabetes).

In an alternative aspect of the invention, there is provided the use of a *Fraxinus angustifolia* extract in the manufacture of a medicament for:
(a) reversing obesity-related and/or metabolic syndrome-related gut microbiota dysbiosis;
(b) treating or preventing hepatic steatosis, non-alcoholic fatty liver disease (NAFLD) and/or non-alcoholic steatohepatitis (NASH);
(c) treating or preventing leaky gut and/or intestinal hyperpermeability;
(d) treating or preventing gut microbiota dysbiosis-induced cardiovascular diseases and/or cardiometabolic diseases;
(e) treating or preventing low grade inflammation;
(f) treating or preventing atherosclerosis;
(g) treating or preventing obesity; and/or
(h) treating or preventing insulin resistance, glucose intolerance, prediabetes, and/or diabetes (such as type 2 diabetes).

In further alternative aspect of the invention, there is provided a method for:

(a) reversing obesity-related and/or metabolic syndrome-related gut microbiota dysbiosis;
(b) treating or preventing hepatic steatosis, non-alcoholic fatty liver disease (NAFLD) and/or non-alcoholic steatohepatitis (NASH);
(c) treating or preventing leaky gut and/or intestinal hyperpermability;
(d) treating or preventing gut microbiota dysbiosis-induced cardiovascular diseases and/or cardiometabolic diseases;
(e) treating or preventing low grade inflammation;
(f) treating or preventing atherosclerosis;
(g) treating or preventing obesity; and/or
(h) treating or preventing insulin resistance, glucose intolerance, prediabetes, and/or diabetes (such as type 2 diabetes), comprising the administration of a therapeutically effective amount of a *Fraxinus angustifolia* extract to a subject in need thereof.

In particular embodiments, the disease or disorder to be reversed, treated or prevented is selected from the group(s) consisting of:

obesity-related gut microbiota dysbiosis, metabolic syndrome-related gut microbiota dysbiosis; and/or hepatic steatosis, non-alcoholic fatty liver disease (NAFLD) and non-alcoholic steatohepatitis (NASH).

As used herein, the term "treatment" (and, similarly, "treating") takes its normal meaning in the field of medicine. In particular, the term may refer to achieving a reduction in the severity of one or more clinical symptom associated with the disease or disorder (e.g. the fungal infection), as may be determined using techniques known to those skilled in the art (for example, by a medical physician) and/or to slowing the progression of the disease or disorder (i.e. increasing the amount of time taken for the disease or disorder to progress to a more severe state, e.g. when compared to the time expected to be taken in a patent not so treated).

As used herein, the term "prevention" (and, similarly, "preventing") includes references to the prophylaxis of the disease or disorder (and vice-versa). In particular, the term may refer to achieving a reduction in the likelihood of the patient (or healthy subject) developing the condition (for example, at least a 10% reduction, such as at least a 20%, 30% or 40% reduction, e.g. at least a 50% reduction).

For the avoidance of doubt, in the context of the present invention, the terms "treating" and "preventing" include the therapeutic, or palliative, treatment of subjects/patients in need of, as well as the prophylactic treatment and/or diagnosis of patients which are susceptible to, the relevant disease states.

As used herein in relation to medical conditions, the term "reducing" may refer to making the observed quantity smaller or decrease in size.

As used herein in relation to medical conditions, the term "reversing" may refer to returning the relevant feature towards a normal state, as known to those skilled in the art. For example, reversing various types of gut microbiota dysbiosis may refer to altering the levels and/or nature of gut microbiota to levels and/or a nature that is that same as, or more similar to, those that the skilled person would expect to observe in a healthy subject.

For the avoidance of doubt, in particular embodiments the *Fraxinus angustifolia* extract comprises (or consist essentially/consist of):

(i) from about 1% to about 15% by weight of nuzhenide;
(ii) from about 1% to about 17% by weight of GL3;
(iii) from about 0.5% to about 1% by weight of oleoside methyl ester;
(iv) from about 0.03% to about 0.12% by weight of excelside B;
(v) from about 0.1% to about 1.7% by weight of GL5; and
(vi) from about 0.08% to about 0.7% by weight of salidroside.

In particular, the FA extract may comprise (or consist essentially/consist of) about 10% by weight nuzhenide and about 10% by weight GI3.

Moreover, for the avoidance of doubt, the *Fraxinus angustifolia* extract may be in the form of a composition (e.g. a pharmaceutical composition or food composition) as described herein.

As used herein, the terms "subject" and "patient" may be used interchangeably and include mammalian species (particularly humans).

As used herein, the term "therapeutically effective amount" may refers to an amount of the extract of the invention, or composition comprising the LA extract of the invention, which confers a therapeutic effect on the treated patient (e.g. an amount sufficient to treat or prevent the disease). The effect may be objective (i.e. measurable by some test or marker) or subjective (i.e. the subject gives an indication of or feels an effect).

As described herein, changes in the composition of the gut microbiota, such as an alteration of the typical ecological organization of the gut microbiota (dysbiosis), are related to conditions such as obesity, insulin resistance, glucose intolerance, prediabetes, diabetes, hepatic steatosis, non-alcoholic fatty liver disease, low grade inflammation, leaky gut, intestinal hyperpermability, gut microbiota dysbiosis-induced cardiovascular diseases, cardiometabolic diseases and atherosclerosis. The potential for restoration of an optimal intestinal microbial system therefore provides a strategy for preventing steatosis progression and the progression of NAFLD to NASH. Moreover, this effect may also be useful in the promotion of general health in patients who are not suffering from a particular medical disease or disorder.

Thus, in particular embodiments, the use (including the extract for use) or method as described herein may comprise (or consist of) delaying or arresting (which latter term may be referred to as halting or preventing) steatosis progression; particularly delaying or arresting (e.g. delaying) the progression of NAFLD to NASH.

As used herein, references to arresting the progression of a disease state will refer to treating that disease such that the skilled person is not able to observe any significant worsening of that disease during a period of time after commencement of such treatment and/or during which such treatment is provided. Similarly, references to arresting the progression of one (first) disease state to another (second) disease state will refer to treating that first disease such that the skilled person is not able to observe the onset of the second disease state during a period of time after commencement of such treatment and/or during which such treatment is provided.

As used herein, references to delaying the progression of a disease state will refer to treating that disease such that the skilled person can observe that, after commencement of such treatment and/or during which such treatment is provided, the time taken for the disease state to worsen is longer (i.e. by a medically significant period of time, such as by at least one week or, particularly, at least four or eight weeks) than that which would be expected if such treatment had not been performed. Similarly, references to delaying the progression of one (first) disease state to another (second) disease state will refer to treating that first disease such that the skilled person can observe that, after commencement of such treatment and/or during which such treatment is provided, the time taken for the first disease state to progress to the second disease state is longer than that which would be expected if such treatment had not been performed.

Moreover, in another aspect of the invention, there is provided the use (e.g. the non-therapeutic use) of a *Fraxinus angustifolia* extract (i.e. an extract of the invention) in:
(i) modulating or adjusting gut microbiota;
(ii) reducing body fat; and/or
(iii) reducing blood glucose concentration.

In an alternative aspect the invention, there is provided a method (e.g. a non-therapeutic method) of:
(i) modulating or adjusting gut microbiota;
(ii) reducing body fat; and/or
(iii) reducing blood glucose concentration,
comprising the administration of an effective amount of a *Fraxinus angustifolia* extract to a subject in need thereof.

As used herein, the terms "modulate" (or "modulating") or "adjust" (or "adjusting") may refer to increasing (enriching) and/or decreasing certain taxonomic groups (phylum, class, order, family, and genus) present in the gut. For example, the reference to modulating or adjusting may refer to an effect that increases and/or decreases certain operational taxonomic units (OTU) present in the gut.

The term "effective amount" refers to an amount of the extract of the invention, or composition comprising the extract of the invention, which confers an effect on the subject to which the extract or composition has been administered (e.g. an amount sufficient to cause the desired effect, such as increasing and/or decreasing certain taxonomic groups (phylum, class, order, family, and genus) present in the gut). The effect may be objective (i.e. measurable by some test or marker) or subjective (i.e. the subject gives an indication of or feels an effect).

As described herein, the use or method may result in increasing and/or decreasing certain taxonomic groups (phylum, class, order, family, and genus) present in the gut, such as increasing (enriching) and/or decreasing certain operational taxonomic units (OTU) present in the gut.

In particular embodiments, the modulating or adjusting refers to:
increasing the levels of bacterial groups selected from the genus consisting of *Burkholderiales, Sutterellacae, Parasutterella, Betaproteobacteria* and *Enterorhabdus*; and/or
reducing the levels of bacterial groups selected from the genus consisting of *Prevotellaceae, Flavonifractor, Clostridium* IV and *Butyricicoccus*.

In more particular embodiments, the modulating or adjusting refers to increasing the level of bacterial groups selected from the families consisting of Coriobacteriaceae, Lactobacillaceae and Rikenellaceae.

In yet more particular embodiments, the modulating or adjusting refers to:
increasing the levels of bacterial groups selected from the genus consisting of Coriobacteriaceae *Olsenella*, Lactobacillaceae *Lactobacillus* and Rikenellaceae *Alistipes*; and/or
reducing the levels of Ruminococcaceae *Butyricicoccus*.

As the presence of certain bacterial taxonomic groups are linked with high levels of steatosis in the liver, the enrichment of certain bacterial taxonomic groups resulting from modulation or adjustment by the extract of the invention, or composition comprising the extract of the invention, may reduce or prevent the development or progression of steatosis in the liver and/or the progression of NAFLD to NASH.

Thus, in particular embodiments the modulating or adjusting gut microbiota is for use in (i.e. results in or has the effect of) preventing or treating non-alcoholic fatty liver disease (NAFLD) and/or delaying (or arresting) the progression of NAFLD to non-alcoholic steatohepatitis (NASH).

In a further aspect of invention, there is provided a method of modulating or adjusting gut microbiota in order to prevent or treat NAFLD and/or delay (or arrest) the progression of NAFLD to NASH comprising the administration of an effective amount of a *Fraxinus angustifolia* extract to a subject in need thereof.

The preventing or treating non-alcoholic fatty liver disease (NAFLD) and/or delaying (or arresting) the progression of NAFLD to non-alcoholic steatohepatitis (NASH) may be achieved by:
increasing the levels of bacterial groups selected from the genus consisting of *Burkholderiales, Sutterellacae, Parasutterella, Betaproteobacteria* and *Enterorhabdus*; and/or
reducing the levels of bacterial groups selected from the genus consisting of *Prevotellaceae, Flavonifractor, Clostridium* IV and *Butyricicoccus*; and/or
by increasing the level of bacterial groups selected from the families consisting of Coriobacteriaceae, Lactobacillaceae and Rikenellaceae; and/or
by increasing the levels of bacterial groups selected from the genus consisting of Coriobacteriaceae *Olsenella*, Lactobacillaceae *Lactobacillus* and Rikenellaceae *Alistipes*; and/or
reducing the levels of Ruminococcaceae *Butyricicoccus*

BRIEF DESCRIPTION OF THE FIGURES

FIG. 3 depicts: (A) liver section prepared from frozen liver and stained with oil red O of control and *Fraxinus angustifolia* treated mice (magnification ×20); and (B) fat percentage by area; Oil red O-stained slides were analyzed with ImageJ analysis software to obtain a quantitative histologic measurement of steatosis; a histogram of pixel intensity was generated from the image, the area was measured and the results were expressed as fat percentage by area. Data are represented by box plot showing median, first quartile, third quartile, minimum and maximum.
** indicates the result is statistically different from control, $p=0.004$ (Mann-Whitney test)

*Fraxinus angustifolia* extract treated mice (HFD60+*F. angust*) at 1 month (_T1) or 3 months (_T3).

Figure 5:
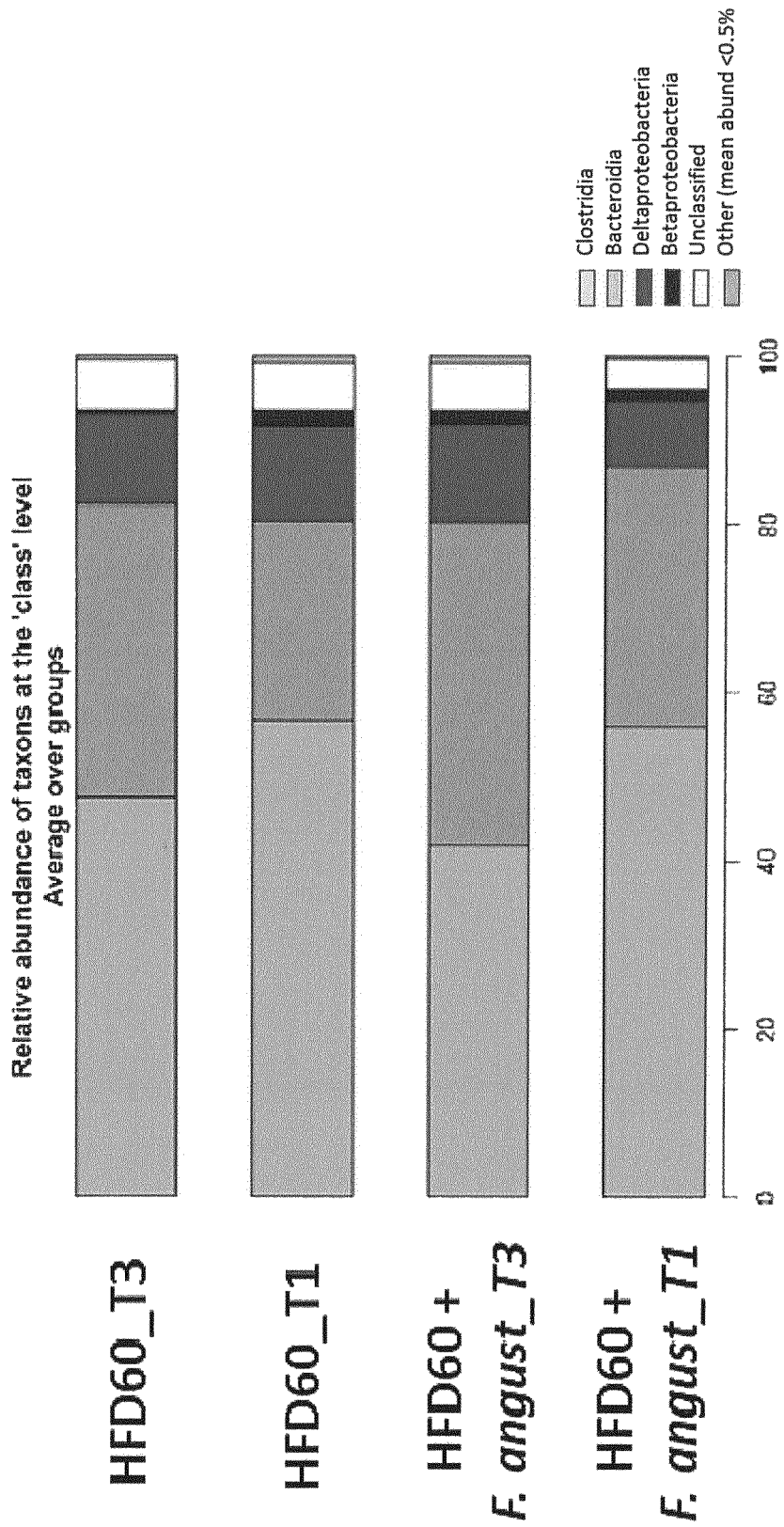

FIG. 5 depicts relative proportion of taxonomic groups at the class level showing the average for each sample type per group: High fat diet treated mice (HFD60) at 1 month (_T1) or 3 months (_T3) or High fat diet and *Fraxinus angustifolia* extract treated mice (HFD60+*F. angust*) at 1 month (_T1) or 3 months (_T3).

Figure 6:
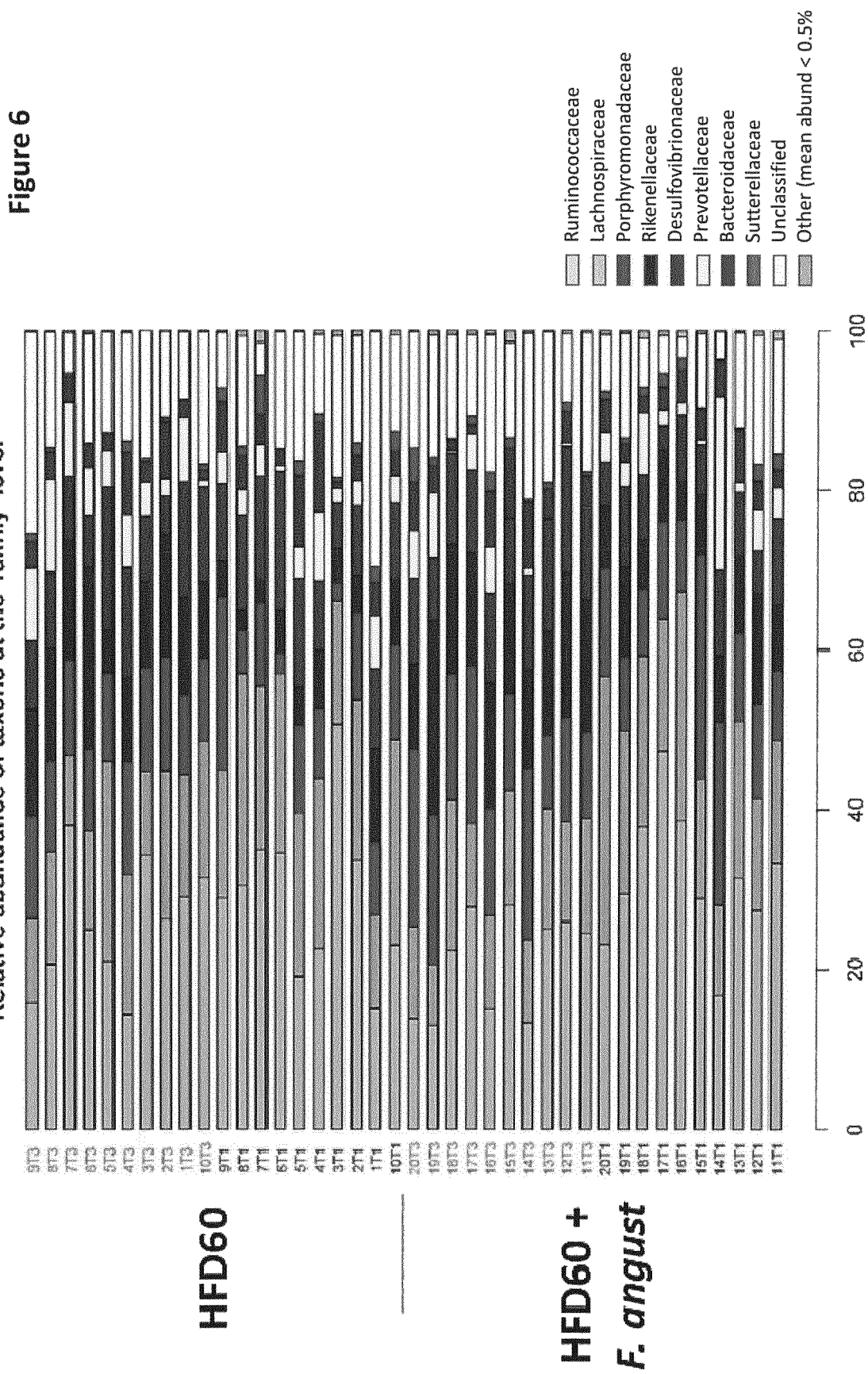

FIG. 6 depicts relative proportion of taxonomic groups at the family level showing individual study samples for each sample type per group: High fat diet treated mice (HFD60) at 1 month (_T1) or 3 months (_T3) or High fat diet and *Fraxinus angustifolia* extract treated mice (HFD60+*F. angust*) at 1 month (_T1) or 3 months (_T3).

Figure 7:
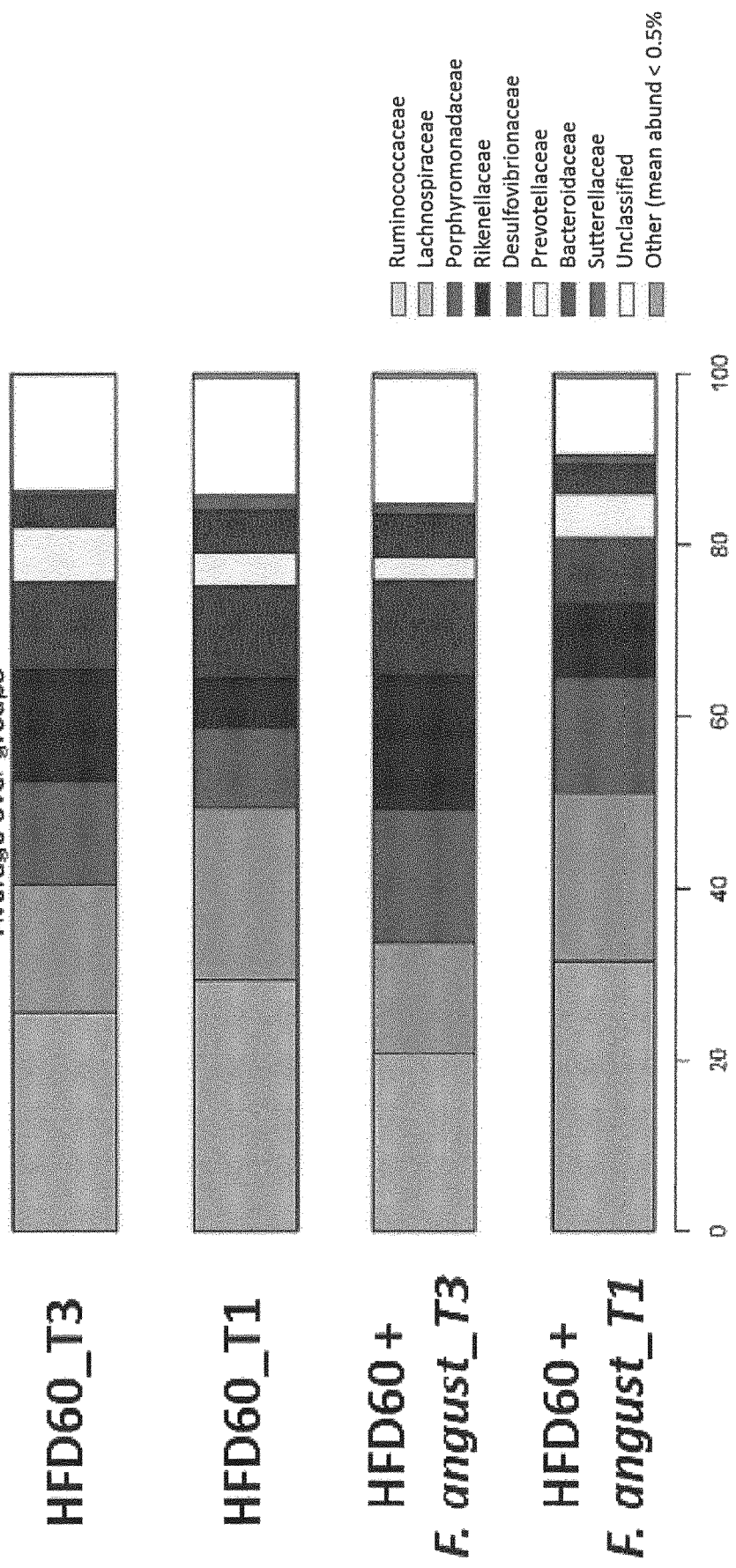

FIG. 7 depicts relative proportion of taxonomic groups at the family level showing the average for each sample type per group: High fat diet treated mice (HFD60) at 1 month (_T1) or 3 months (_T3) or High fat diet and *Fraxinus angustifolia* extract treated mice (HFD60+*F. angust*) at 1 month (_T1) or 3 months (_T3).

Figure 8:
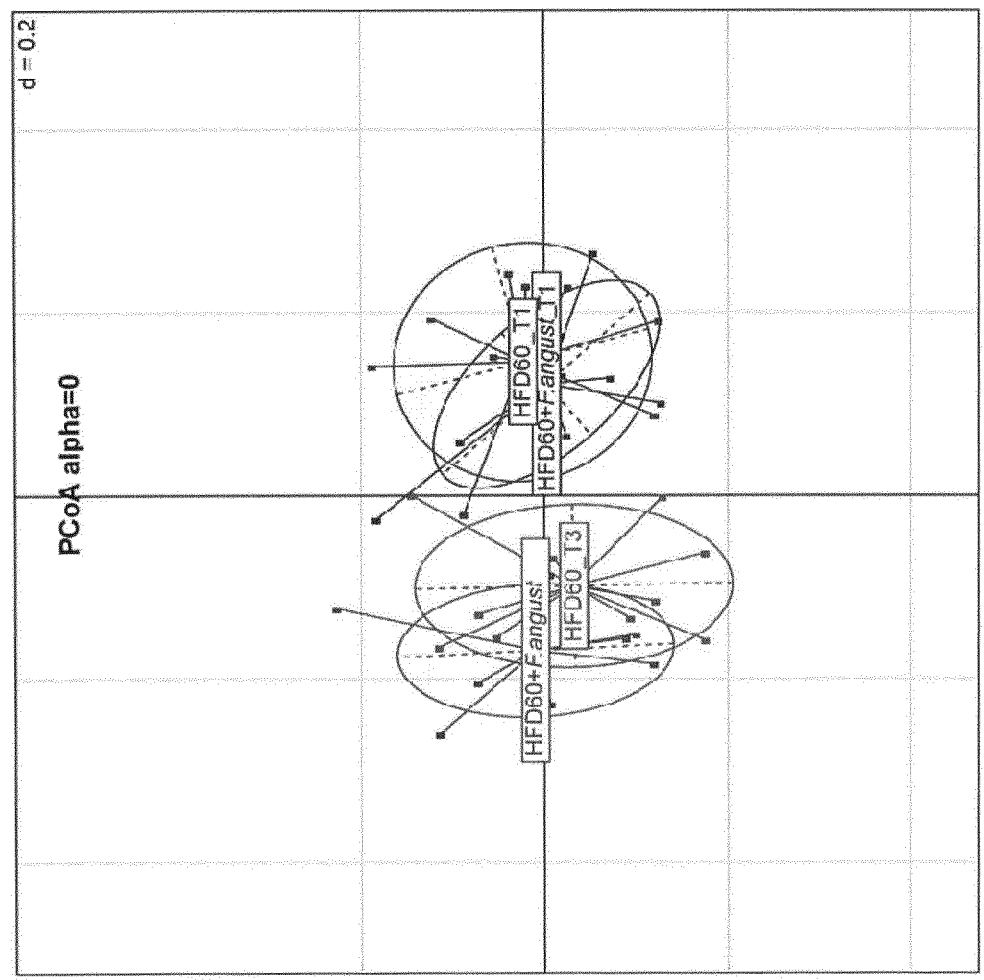
Figure 9:
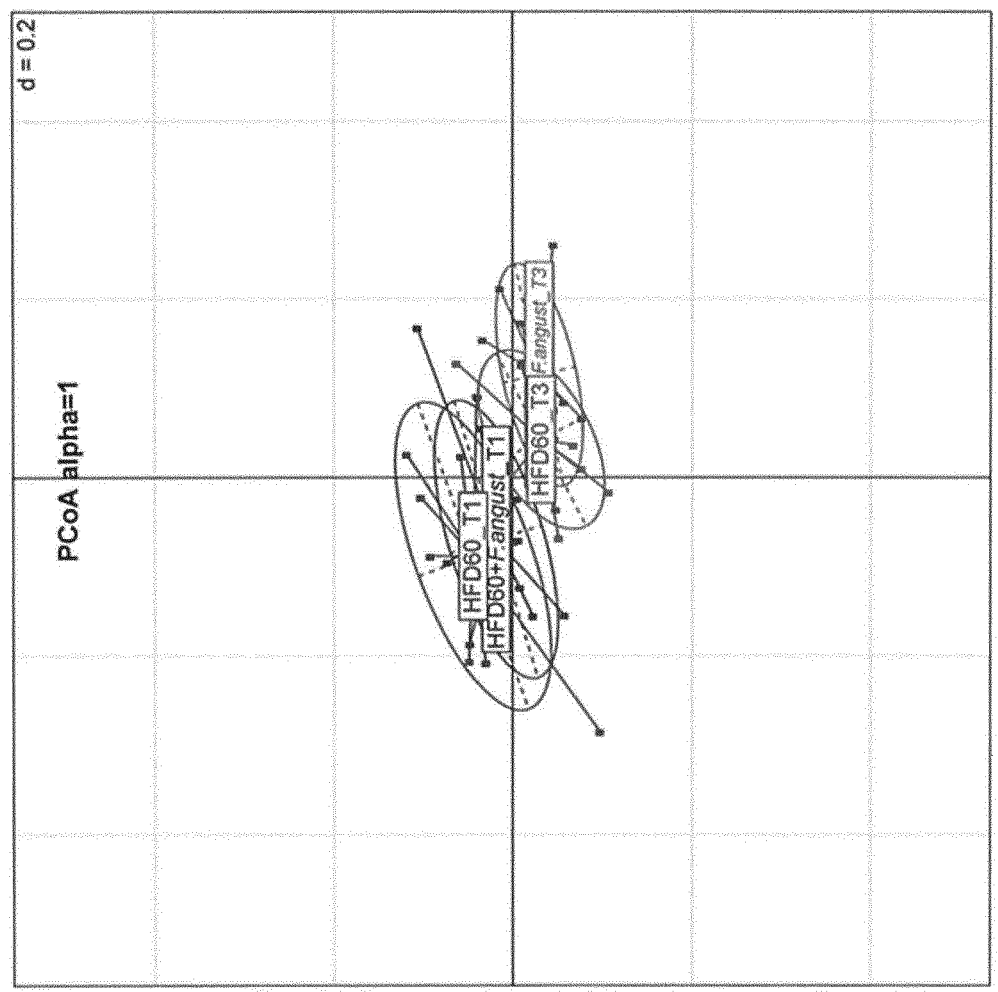

FIGS. 8 and 9 depict Principal Coordinate Analysis (PCoA) to compare samples from the different groups of mice (high fat diet treated mice (HFD60) at 1 month (_T1) or 3 months (_T3) or High fat diet and *Fraxinus angustifolia* extract treated mice (HFD60+*F. angust*) at 1 month (_T1) or 3 months (_T3)) based on the Generalized UniFrac distance metrics. Both PCoA plots with alpha values of 0 and 1 are shown.

Figure 10:
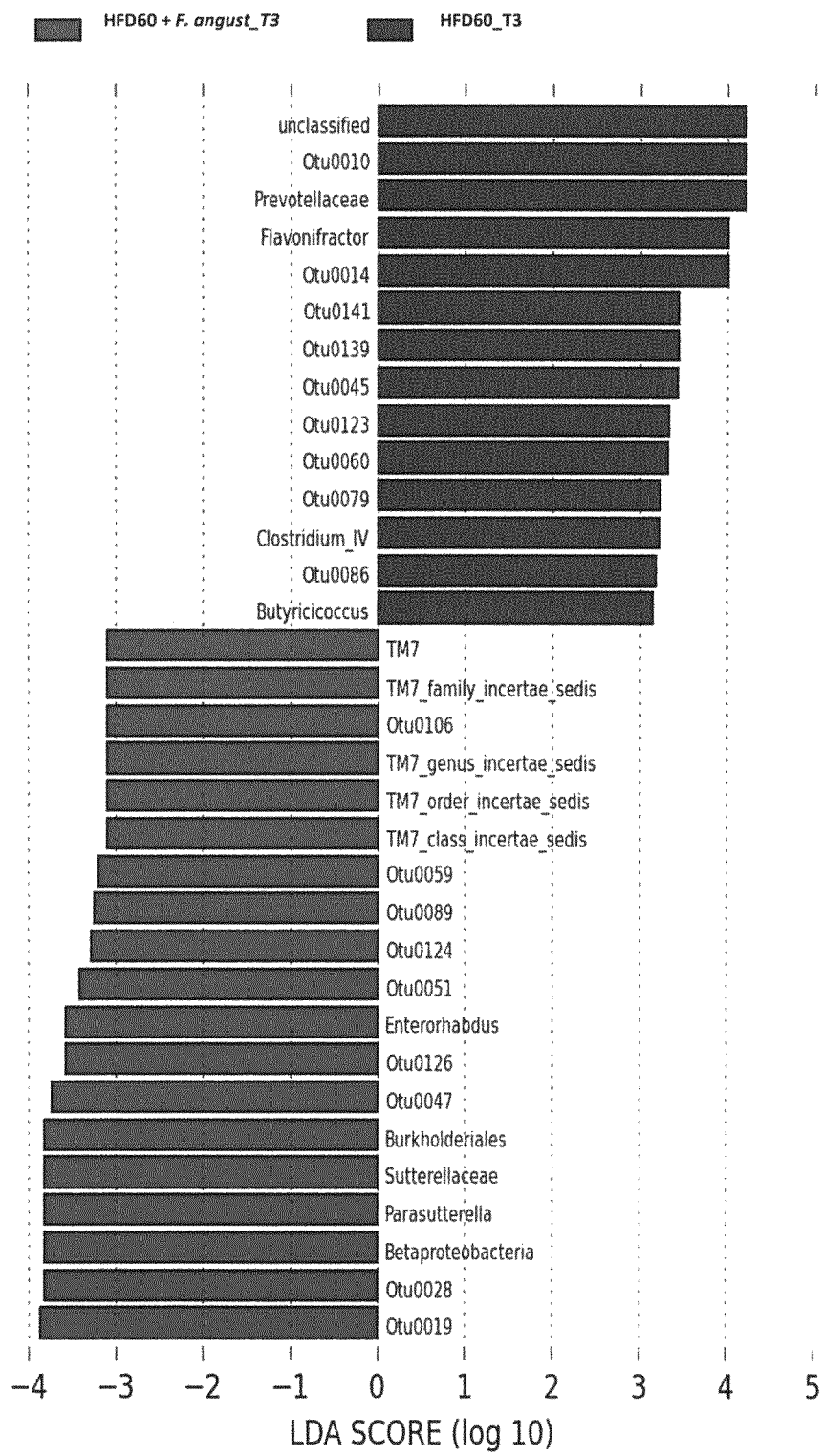

FIG. 10 depicts comparison at 3 months between mice fed a high fat diet without supplementation and mice fed a high fat diet with supplementation with *Fraxinus angustifolia* extract. The linear discriminant analysis effect size was determined using default values (alpha value of 0.5 for both the factorial Kruskal-Wallis test among classes and the pairwise Wilcoxon test between subclasses, threshold of 2.0 for the logarithmic LDA score for discriminative features) and the strategy for multi-class analysis set to 'all-against-all'. (B) LEfSe cladogram from the LDS effect size data were generated with Bacteria as the tree root with six genus maximum taxonomic levels. The highlights (green or red) represent enrichment of the indicated taxonomic groups in the corresponding group.

Figure 11:
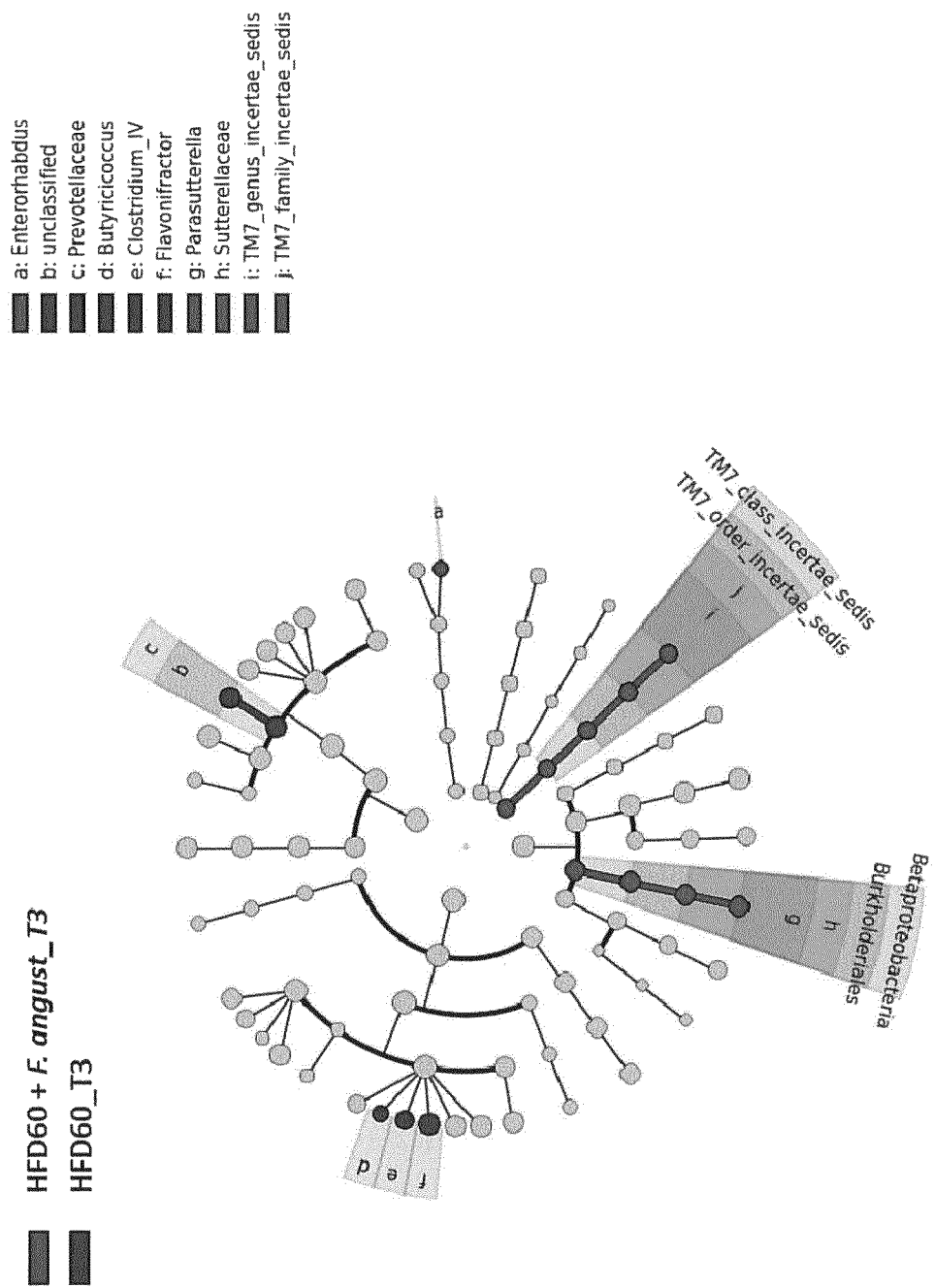

FIG. 11 depicts comparison at 3 months between mice fed a high fat diet without supplementation and mice fed a high fat diet with supplementation with *Fraxinus angustifolia* extract. LEfSe cladogram from the LDS effect size data were generated with Bacteria as the tree root with six genus maximum taxonomic levels. The highlights (green or red) represent enrichment of the indicated taxonomic groups in the corresponding group.

Figure 13:
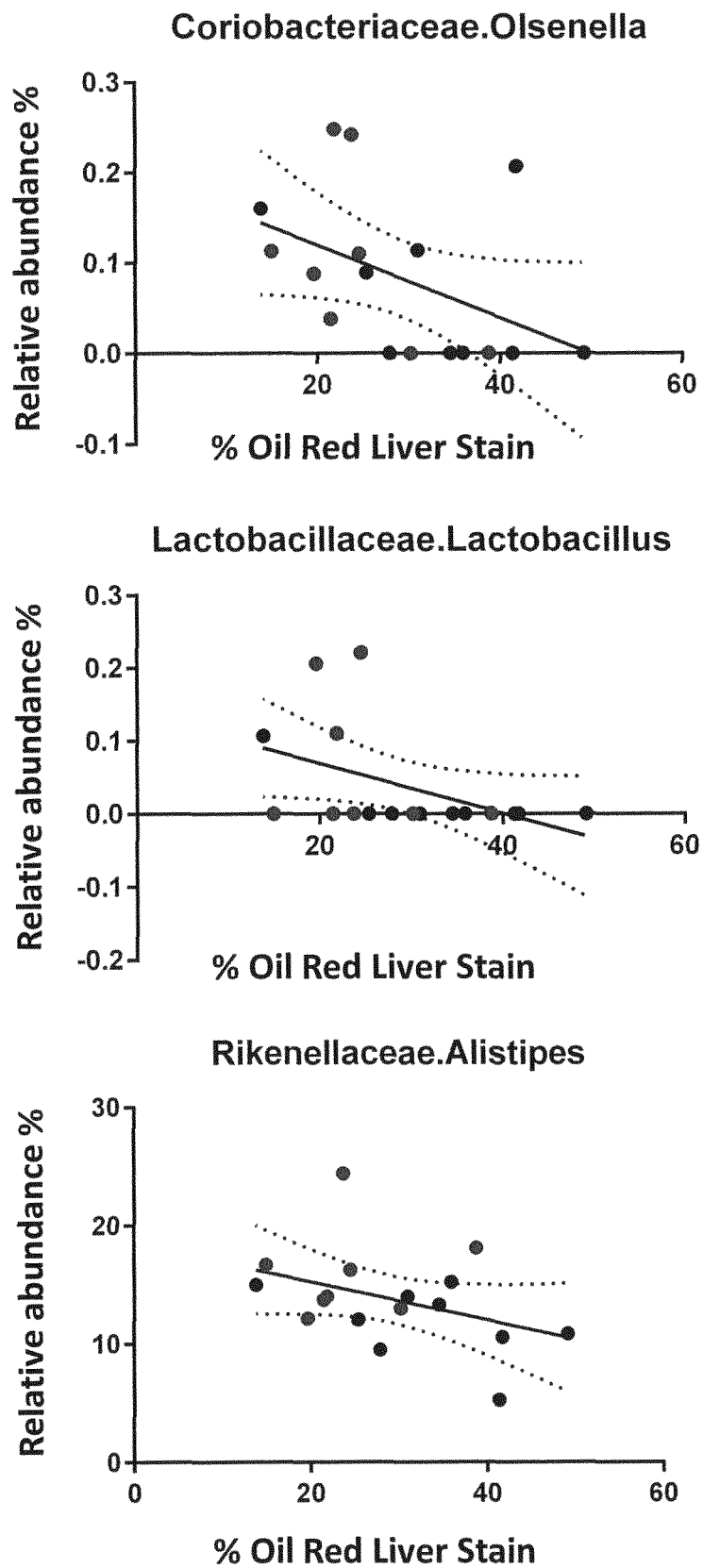
Figure 14:
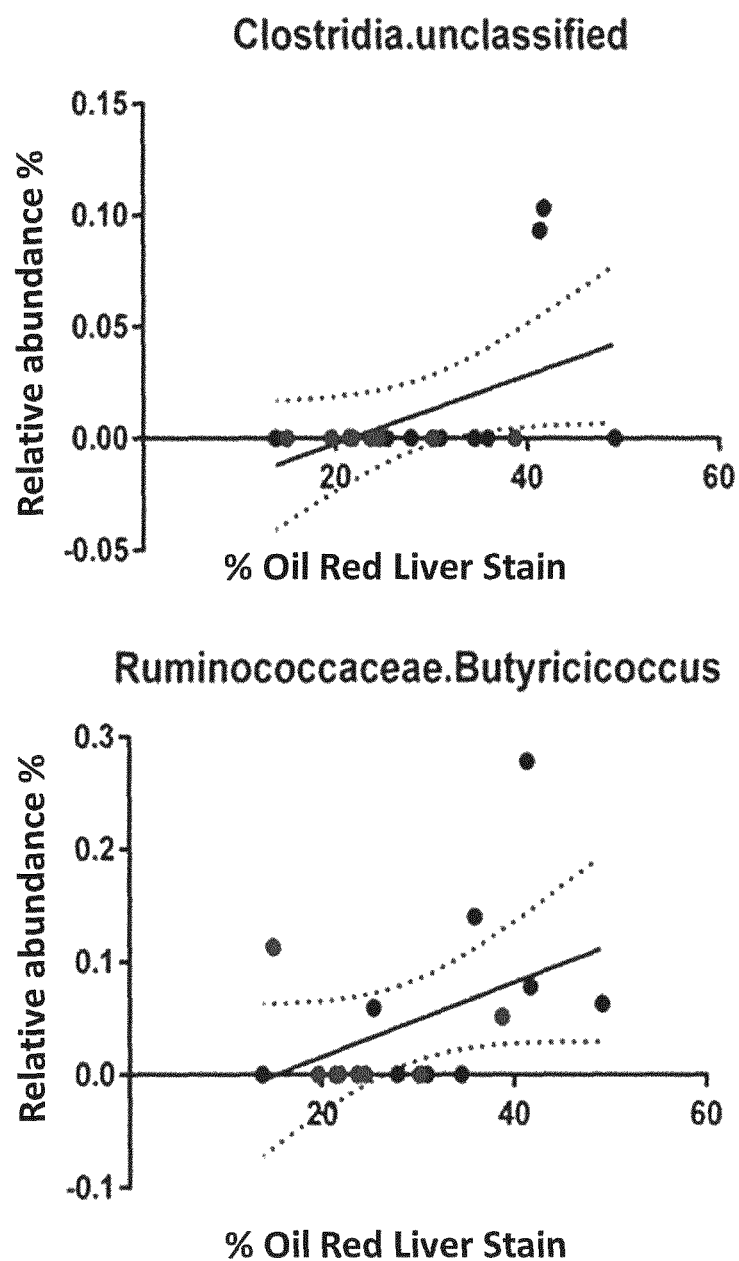

FIGS. 12, 13 and 14 depict regression analyses of Random Forest Identified Family taxonomic groups and the O red oil liver stain percentage as steatosis severity.

The present invention will be further described by reference to the following, non-limiting examples.

EXAMPLES

Example 1—Extraction of *Fraxinus angustifolia* with Water

A total of 2.5 kg of the samara of *F. angustifolia* were dried in air and then ground into coarse powder with a particle size approximately 1-2 mm. The coarse powder was soaked in water in a percolator at 80-90° C. for 5 hours and the water extract was drained from the percolator. The extraction process was repeated three times. All the water extracts were combined together and concentrated in a rotary vacuum evaporator. After water was evaporated, a total of 550 grams of dried powdered extract was obtained. The HPLC analysis indicates that this powdered extract contained two major secoiridoids, 11.4% (weight/weight) of nuzhenide and 6.2% of GB. The composition also contained 0.19% oleoside-1 1-methyl ester, 0.41% excelside B, 0.63% GI5, 0.2% salidroside, together with some minor secoiridoids including, ligstroside, oleoside dimethyl ester, and excelside A.

Example 2—Extraction of *Fraxinus angustifolia* with Water, Water-EtOH, and EtOH 5 samples were prepared and each sample contained 5 grams of *F. angustifolia* samara. Each sample was milled into powder and was subjected to solvent extraction with 200 niL of water, 25% EtOH/75% water, 50% EtOH/50% water, 75% EtOH/25% water, and EtOH, respectively. After extraction for 24 hours at room temperature (22-24° C.), the solvents were evaporated and the residual solids were analyzed by HPLC. The secoiridoid contents and salidroside are listed in Table 1.

TABLE 1

Major secoiridoid contents and salidroside using different solvents (results expressed as percent by weight)

| Compounds | EtOH | 75% EtOH | 50% EtOH | 25% EtOH | water |
|---|---|---|---|---|---|
| Nuzhenide | 9.05 | 15.04 | 15.43 | 14.10 | 1.50 |
| GI 3 | 9.20 | 14.77 | 17.06 | 9.18 | 1.14 |
| Oleoside dimethyl ester | 0.57 | 0.91 | 0.78 | 0.74 | 0.96 |
| Excelside B | 0.06 | 0.09 | 0.10 | 0.12 | 0.03 |
| GI 5 | 0.91 | 1.45 | 1.70 | 0.83 | 0.10 |
| Salidroside | 0.08 | 0.17 | 0.16 | 0.18 | 0.74 |

Example 3—Isolation of Secoiridoids from *Fraxinus angustifolia*

3.5 L of methanol were added and mixed with 500 grams of powdered extract obtained from the procedure shown in Example 1, for 3 hours at room temperature. The methanol solution was separated from the powder by a filtration process. The same process was repeated once and the two methanol extracts were combined and concentrated under reduced pressure to yield a total of 54 grams of dried methanol extract. The methanol extract was re-dissolved in water and filtered to remove non-water soluble substances. The filtrate was further subjected to reverse-phase column chromatographic separation over C-18 resin washed with water and gradient MeOH-water solvent system from 10% MeOH in water to 100% MeOH. A total of 7 fractions were collected. Each fraction eluted from column was evaporated under vacuum and combined by HPLC analysis. Fractions 2, 3 and 7 were loaded on a chromatographic column filled with silica gel resin and eluted with chloroform-methanol system started from CHCl$_3$, 10% MeOH/CHCl$_3$, 20% MeOH/CHCl$_3$, to 100% MeOH. Fractions collected from silica gel column were compared by HPLC analysis and each separated eluate was repeatedly subjected to column chromatographies over MCI GEL CHP-20P and/or Sephadex LH-20 resins and eluted with water-methanol system until a single pure compound was obtained. The compounds excelside A, excelside B, nuzhenide, GI3, GI5, ligstroside, oleoside dimethyl ester, oleoside-1,1-methyl ester, and salidroside were identified. All the chemical structures were elucidated by spectroscopic methods.

Example 4—Testing the Effect of *Fraxinus angustifolia* Extract on Liver Steatosis in Mice 9-week-old adult male C57BL/6 mice were purchased from Charles River (Charles River Laboratories, L'Arbresle, Rhône, France) and housed at a constant room temperature and humidity and maintained in a 12/12h light/dark cycle in SPF conditions. They were fed with a high-fat diet (HFD) with 60% energy from fat obtained by SAFE (Scientific Animal Food & Engineering, Augy, France) for 12 weeks and water was given ad libitum. Tables 2 and 3 give the list of ingredients and the nutritional values of the HFD respectively.

TABLE 2

List of ingredients of the Purified Diet 260HF diet from SAFE (Augy, France)

| Purified Diet 260HF | Quantity (g) |
| --- | --- |
| Casein | 22.800 |
| DL-methionine | 0.200 |
| Maldodextrin | 17.015 |
| Sucrose | 16.633 |
| Anhydrous butter | 33.350 |
| Soybean oil | 2.500 |
| Minerals premix AIN93G-mx | 4.550 |
| Sodium bicarbonate | 1.050 |
| Potassium citrate | 0.400 |
| Vitamins premix AIN93G-vx | 1.300 |
| Choline bitartrate | 0.200 |
| Antioxidant | 0.002 |
| Total | 100 |

TABLE 3

Nutritional values of the Purified Diet 260HF diet from SAFE (Augy, France)

| Total energy (kcal/kg) | 5283 |
| --- | --- |
| Energy from protein in kcal/kg (%) | 776 (14.7%) |
| Energy from fat in kcal/kg (%) | 3222 (61%) |
| Energy from carbohydrates | 1285 (24.3%) |

In the treatment group, the *Fraxinus angustifolia* (Vahl) extract was directly mixed in the diet and thus administered through oral route at 200 mg/kg/day, which represents a human equivalent dose of 1 g/day according to the formula from FDA (2005): Human equivalent dose HED (mg/kg) =animal dose in mg/kg×(animal weight in kg/human weight in kg). The dried extract of *Fraxinus angustifolia* samara was obtained by extraction with 30% (v/v) ethanol in water as described herein. The extract can preferably contain approximately 10% (% w/w) of nuzhenide and GL3 based on the total dry weight of the herbal extract. The effect of *Fraxinus angustifolia* (Vahl) extract consumption was analysed by comparing the different parameters in rats consuming both the HFD and the extract (*F. angustifolia* group) in comparison to rats consuming the HFD alone (control group).

Body weight and body weight gain was followed during the 12 weeks and body composition (percentage of fat mass, lean mass and water) was evaluated by NMR at the end of treatment. An oral glucose tolerance test (OGTT) was done after the 12 weeks of treatment by administrating 2 g per kg body weight of glucose in fasted mice and by following glycaemia during the 2 hours following glucose administration.

At sacrifice, liver was carefully removed, weighted and conditioned for both histological analyses. For the detection of lipid deposition in liver, liver section were prepared from frozen liver and stained with oil red O as previously reported (Fowler, S. D., Greenspan, P., O. *J. Histochem Cytochem*, 33, 833-836 (1985)). Oil red O-stained slides were analyzed with ImageJ analysis software (National Institute of Mental Health, Bethesda, Md., USA) to obtain a quantitative histologic measurement of steatosis. Five random images at ×20 magnification for each liver biopsy were taken to ensure a representative sample for each specimen. A histogram of pixel intensity was generated from the image, the area was measured and the results were expressed as fat percentage by area.

Figure 1:
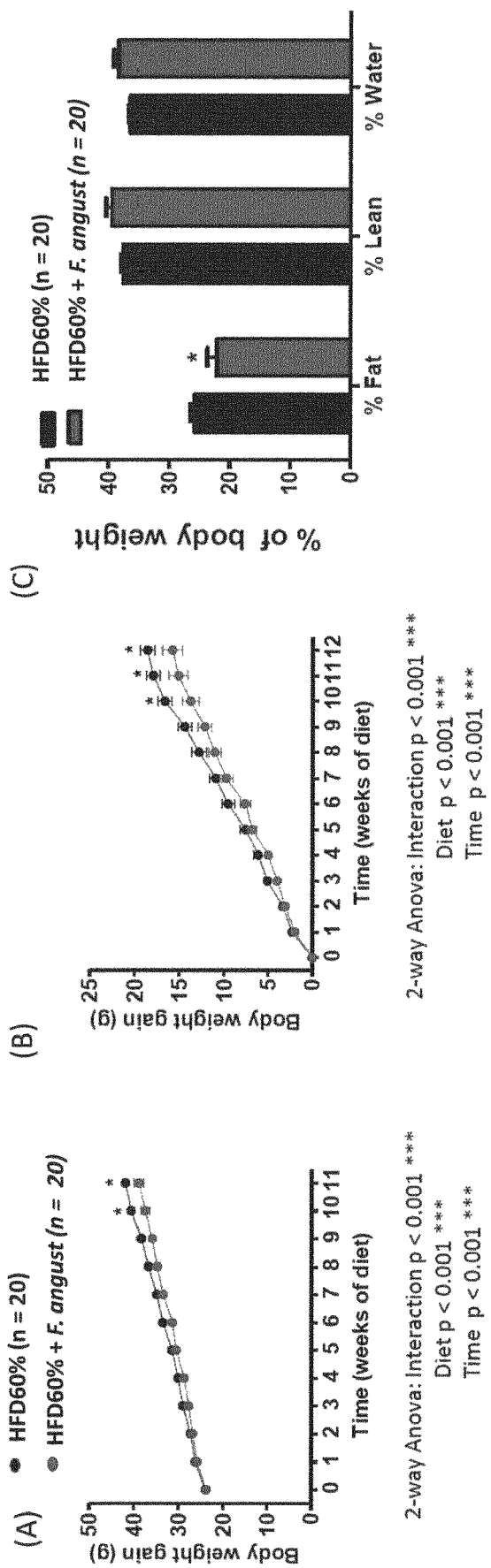
FIG. 1 depicts: (A) body weight, (B) body weight gain of mice during the 12 weeks of consumption of the high fat diet (60%) with or without *Fraxinus angustifolia* extract at 200 mg/kg body weight, and (C) body composition of mice after the 12-week treatment.
* indicates the result is statistically different from control, $p<0.05$.

As shown in FIG. 1, the 12-week consumption of a high fat diet induced a strong body weight gain that was counteracted by the simultaneous consumption of the *Fraxinus angustifolia* extract. Particularly, the *Fraxinus angustifolia* extract was able to reduce fat mass in mice fed a HFD during 12 weeks.

Figure 2:
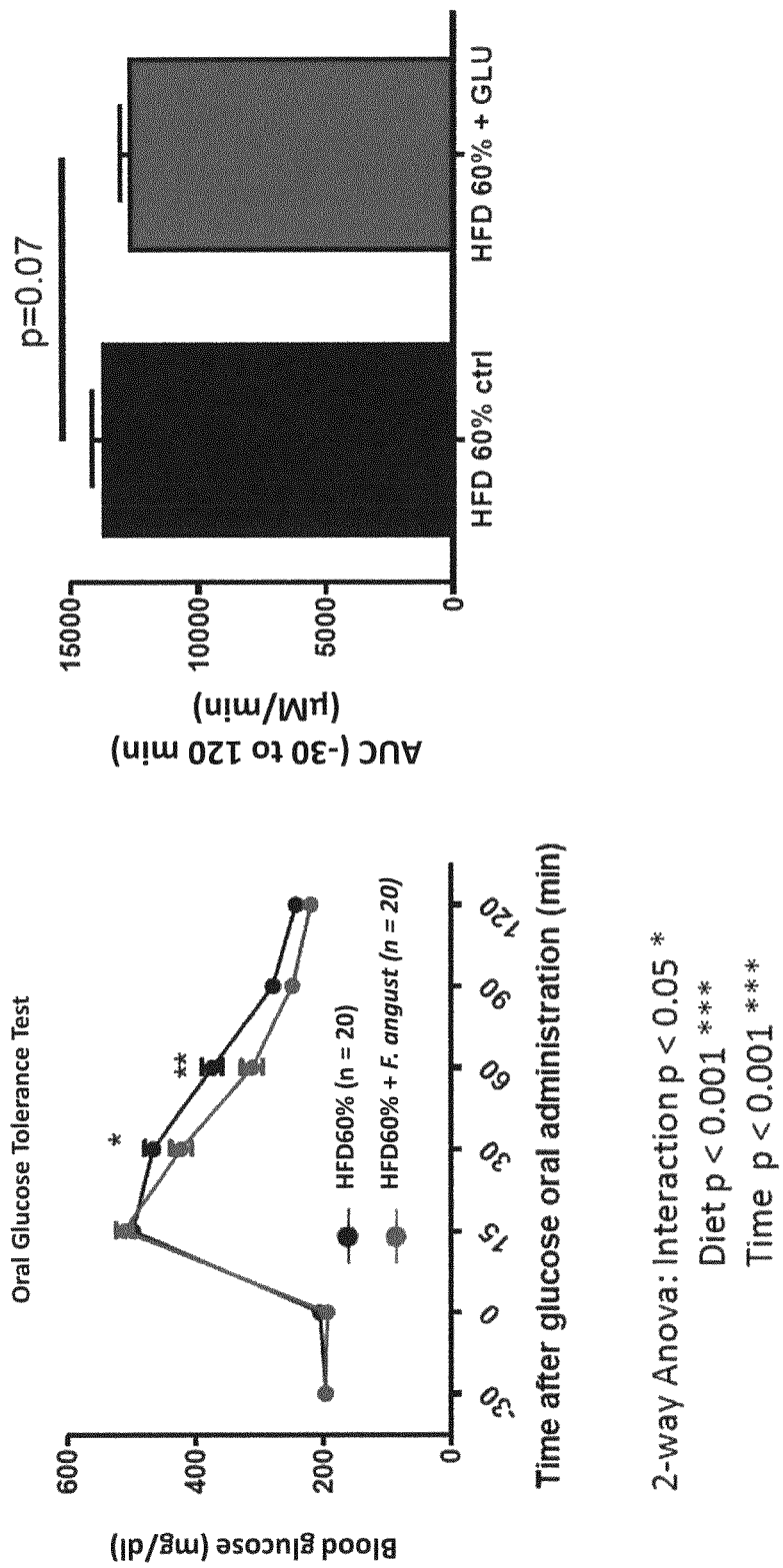
FIG. 2 depicts: (A) Blood glucose before and after 15, 30, 60, 90 and 120 minutes after oral glucose administration by oral gavage and (B) respective Area under the curve (AUC) values of mice at the end of the 12-week consumption of the high fat diet (60%) with or without *Fraxinus angustifolia* extract at 200 mg/kg body weight.
* indicates the result is statistically different from control, $p<0.05$.
Figure 4:
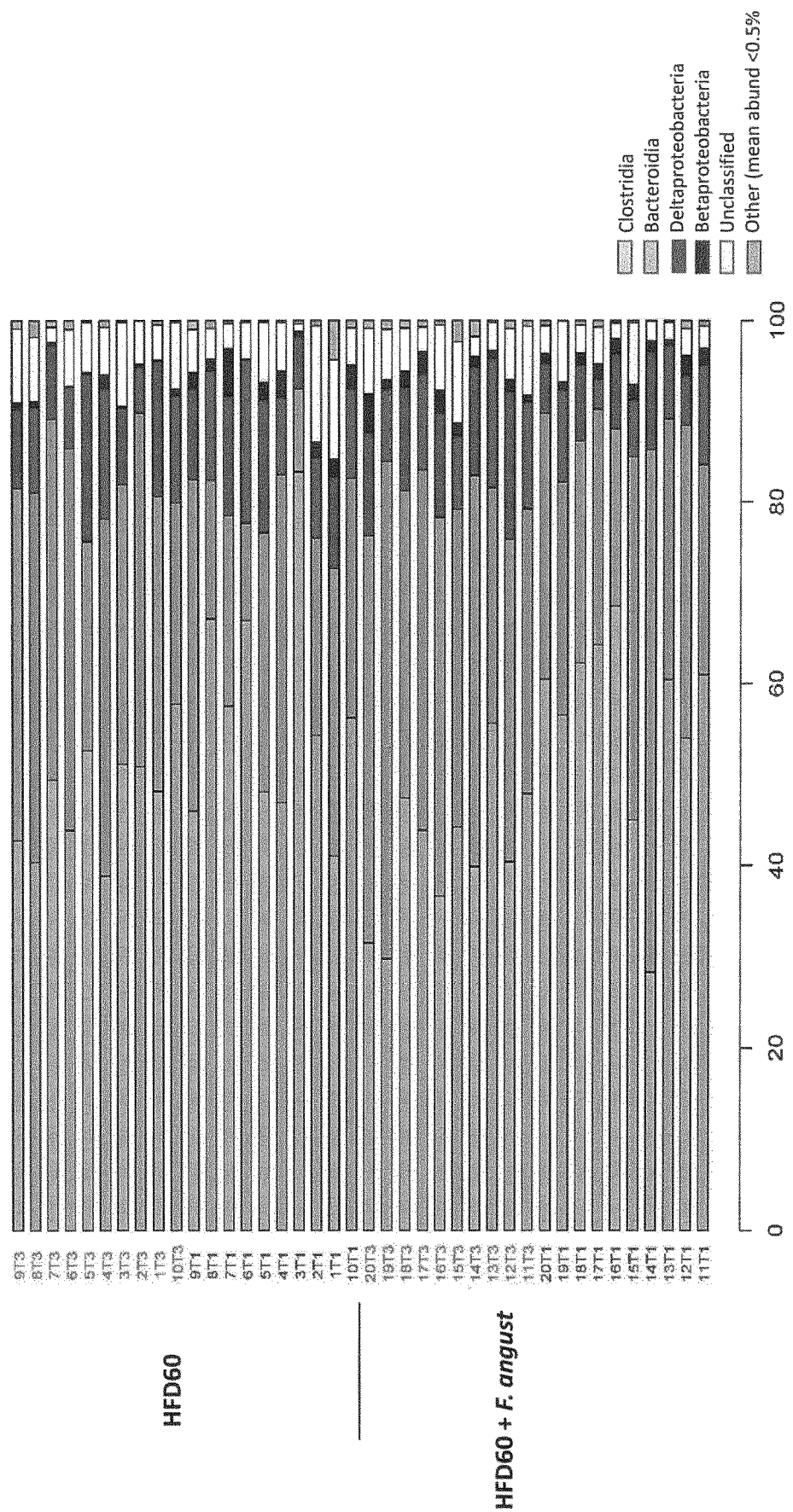
FIG. 4 depicts relative proportion of taxonomic groups at the class level showing individual study samples for each sample type per group: High fat diet treated mice (HFD60) at 1 month (_T1) or 3 months (_T3) or High fat diet.

As shown in FIG. 2, consumption of the *Fraxinus angustifolia* extract was also able to significantly reduce glucose intolerance in mice fed a HFD as shown by the significantly reduced blood glucose concentration 30 and 60 minutes after the glycemic load ($p<0.05$) and by the significant reduction of the area under the (glycaemia versus time) curve (AUC) ($p=0.07$).

As shown in FIG. 3, the 12-week consumption of a high fat diet induced a high level of fat deposit into the liver, i.e steatosis in the control group (35.2%), which is classical with this type of diet as a model of diet induced obesity, diabetes and liver steatosis (see: Takahashi Y, Soejima Y, Fukusato T, *World J Gastroenterol*, 18(19), 2300-2308 (2012); and Zhou, Y. and Xie, L., *Am J Digest Dis*, 2(1), 60-67 (2015)). The 12-week treatment with the *Fraxinus angustifolia* extract was able to significantly reduce the severity of steatosis ($p=0.004$), as only 22.8 percent of fat was found into the liver of mice treated with the extract, which corresponds to a reduction of 35% of steatosis. According to the World Gastroenterology Organisation histological scoring system (2012) and the classification from Kleiner and Brunt (Kleiner, D. E. and Brunt, E. M., *Semin Liver Dis*, 32, 3-13 (2012)), which classify the severity of steatosis according to fat content (Grade 0: <5%, Grade 1: 5-33%, Grade 2: 34-66%, Grade 3: >67%), the treatment with the *Fraxinus angustifolia* warranted the reduction of steatosis severity from grade 2 to grade 1.

Example 5—Testing the Effect of *Fraxinus angustifolia* Extract on Gut Microbiota Dysbosis in Mice In order to evaluate gut microbiota modification induced by *Fraxinus angustifolia* extract consumption in mice fed the high fat diet, a 16S rDNA metagenomics study was performed on murine fecal samples at the beginning (4 weeks) and after 12 weeks of HFD consumption with or without the *Fraxinus angustifolia* extract (10 mice par groups, total number of 40 mice). Bacterial populations contained in the samples were determined using next generation high throughput sequencing of variable regions (V3-V4) of the 16S rDNA bacterial gene.

The metagenomics workflow is used to classify organisms from a metagenomic sample by amplifying specific regions in the 16S ribosomal RNA gene. This metagenomics workflow is exclusive to bacteria. The main output is a classification of reads at several taxonomic levels: phylum, class, order, family and genus. The microbial population present in the samples has been determined using next generation high throughput sequencing of variable regions of the 16S rRNA bacterial gene. The workflow included the following steps:

(1) Library Construction and Sequencing

PCR amplification was performed using 16S universal primers targeting the V3-V4 region of the bacterial 16S ribosomal gene. The joint pair length was set to encompass 476 base pairs amplicon thanks to 2×300 paired-end MiSeq kit V3. For each sample, a sequencing library was generated by addition of sequencing adapters. The detection of the sequencing fragments was performed using MiSeq Illumina® technology.

(2) Bioinformatics Pipeline

The targeted metagenomic sequences from microbiota were analysed using the following bioinformatics pipeline; briefly, after demultiplexing of the bar coded Illumina paired reads, single read sequences were cleaned and paired for each sample independently into longer fragments. After quality-filtering and alignment against a 16S reference database, a clustering into operational taxonomic units (OTU) with a 97% identity threshold, and a taxonomic assignment were performed in order to determine community profiles.

Based on these results, graphical representations were made of the relative proportion of taxonomic groups (phylum, class, order, family, and genus) present in 1) individual study samples and 2) the average for each sample type/group.

As shown in FIGS. 4, 5, 6 and 7, the gut microbiota profiles were similar at the beginning of high fat diet consumption (T1) although some minor differences could be seen at the class and more intensively at the family levels in mice that have consumed the *Fraxinus angustifolia* extract in comparison to mice that have not consumed the extract concomitantly with the HFD.

Principal Coordinate Analysis (PCoA) was performed to compare samples based on the Generalized UniFrac distance metrics (Lozupone C, Lladser M E, Knights D, Stombaugh J, Knight R (2011) UniFrac: an effective distance metric for microbial community comparison. ISME J. 5(2): 169-172) in order to illustrate the differences into groups of mice.

As shown in FIGS. 8 and 9, although the gut microbiota composition of mice were similar at the beginning of high fat diet consumption (T1) as demonstrated by the stackable profiles of the individuals' distribution, it could be seen that after 3 months of treatment with the *Fraxinus angustifolia* extract, treated individuals could be differentiated from untreated individuals according to their gut microbiota composition.

The Linear Discriminant Analysis (LDA) Effect Size (LEfSe) (Segata, N. et al., *Genome Biol*, 12(6), R60 (2011)) method was then used to analyze the high-dimensional class comparisons of the metagenomics data. LefSe is an algorithm for high-dimensional biomarker discovery and explanation that can identify taxonomic groups characterizing the differences between two or more biological conditions. It emphasizes both statistical significance and biological relevance, allowing researchers to identify differentially abundant features that are also consistent with biologically meaningful categories (subclasses). LEfSe first robustly identifies features that are statistically different among biological classes. It then performs additional tests to assess whether these differences are consistent with respect to expected biological behavior. The linear discriminant analysis effect size was determined using default values (alpha value of 0.5 for both the factorial Kruskal-Wallis test among classes and the pairwise Wilcoxon test between subclasses, threshold of 2.0 for the logarithmic LDA score for discriminative features) and the strategy for multi-class analysis set to 'all-against-all'.

As shown in FIGS. 10 and 11, LefSe analysis revealed that, at the genus or OTU levels, there was enrichment of different taxonomic groups (*Burkholderiales, Sutterellacae, Parasutterella, Betaproteobacteria, Enterorhabdus* and other OTUs) in mice treated with the *Fraxinus angustifolia* extract in comparison to untreated mice fed a HFD. Conversely, *Prevotellaceae, Flavonifractor, Clostridium IV, Butyricicoccus* and other taxonomic groups were less represented in mice treated with the *Fraxinus angustifolia* extract in comparison to untreated mice fed a HFD. These results highlight the modification of gut microbiota induced by the *Fraxinus angustifolia* extract supplementation.

Correlation between microbiome analysis and steatosis severity was analysed by using the Random Forest Analysis methodology (Touw, W. G. et al., *Brief Bioinform*, 14(3), 315-26 (2013)). As shown in FIGS. 12, 13 and 14, the relative abundance of several taxonomic groups at the family or the genus level respectively are correlated with the steatosis severity in mice fed a high fat diet, clearly showing that *Fraxinus angustifolia* extract was able to modify the gut microbiota and particularly the relative abundance of some families or genus (Coriobacteriaceae, Lactobacillaceae, Rikenellaceae) and that these modifications could reduce the development of steatosis. The results of the analysis of the correlation between abundance of taxonomic groups (by family and genus) and steatosis severity is shown in Tables 4 and 5 below.

TABLE 4

Statistical analysis for the correlation between abundance of taxonomic groups by Family and steatosis severity.

| | Taxonomic Classification | Random Forest (increased mean square error) | Spearman r | P (two-tailed) |
|---|---|---|---|---|
| Family | Actinobacteria\|Actinobacteria\|Coriobacteriales\|Coriobacteriaceae | 7.98 | −0.47 | 0.05 |
| Family | Fimicutes\|Bacilli\|Lactobacillales\|Lactobacillaceae | 2.98 | −0.53 | 0.03 |
| Family | Bacteroidetes\|Bacteroidia\|Bacteroidales\|Rikenellaceae | 4.02 | −0.40 | 0.11 |
| Family | Firmicutes\|Clostridia\|unclassified\|unclassified | 1.04 | 0.49 | 0.05 |

TABLE 5

Statistical analysis for the correlation between abundance of taxonomic groups by Genus and steatosis severity.

| Taxonomic Classification | Random Forest (increased mean square error) | Spearman r | P (two-tailed) |
|---|---|---|---|
| Genus *Actinobacteria\Actinobacteria\Coriobacteriales\Coriobacteriaceae* | 9.33 | −0.51 | 0.04 |
| Genus *Fimicutes\Bacilli\Lactobacillales\Lactobacillaceae* | 0.88 | −0.53 | 0.03 |
| Genus *Bacteroidetes\Bacteroidia\Bacteroidales\Rikenellaceae* | 2.73 | −0.40 | 0.12 |
| Genus *Firmicutes\Clostridia\unclassified\unclassified\unclassified* | 0.14 | 0.49 | 0.04 |
| Genus *Firmicutes\Clostridia\Clostridiales\Ruminococcaceae\Butyricicoccus* | 1.84 | 0.51 | 0.04 |

The invention claimed is:

1. A method for:
   (a) reversing metabolic syndrome-related gut microbiota dysbiosis;
   (b) treating hepatic steatosis, non-alcoholic fatty liver disease (NAFLD) and/or non-alcoholic steatohepatitis (NASH);
   (c) treating gut microbiota dysbiosis-induced cardiovascular diseases and/or cardiometabolic diseases; and/or
   (d) delaying the progression of non-alcoholic fatty liver disease (NAFLD) and non-alcoholic steatohepatitis (NASH);
   comprising the administration of a therapeutically effective amount of a *Fraxinus angustifolia* samara extract to a subject in need thereof, wherein the extract comprises:
   (i) from about 1% to about 16% by weight of nuzhenide;
   (ii) from about 1% to about 18% by weight of GL3;
   (iii) oleoside methyl ester;
   (iv) excelside B;
   (v) GL5; and
   (vi) salidroside.

2. The method according to claim 1, wherein a disease or disorder to be reversed, treated, or delayed is selected from the group consisting of: metabolic syndrome-related gut microbiota dysbiosis; and/or hepatic steatosis, non-alcoholic fatty liver disease (NAFLD) and non-alcoholic steatohepatitis (NASH).

3. A method of modulating or adjusting gut microbiota for treating non-alcoholic fatty liver disease (NAFLD) and/or delaying the progression of non-alcoholic fatty liver disease (NAFLD) and non-alcoholic steatohepatitis (NASH) comprising the administration of an effective amount of a *Fraxinus angustifolia* samara extract to a subject in need thereof, wherein the extract comprises:
   (i) from about 1% to about 16% by weight of nuzhenide;
   (ii) from about 1% to about 18% by weight of GL3;
   (iii) oleoside methyl ester;
   (iv) excel side B;
   (v) GL5; and
   (vi) salidroside.

4. The method according to claim 3, wherein the modulating or adjusting increases bacterial groups selected from the genus consisting of *Betaproteobacteria* and *Enterorhabdus*.

5. The method according to claim 3, wherein the modulating or adjusting increases bacterial groups selected from the genus consisting of *Prevotellaceae, Flavoifractor, Clostridium IV* and *Butyricicoccus*.

6. The method according to claim 3, wherein the modulating or adjusting increases bacterial groups selected from the families comprising Coriobacteriaceae, Lactobacillaceae and Rikenellaceae.

7. The method according to claim 1, wherein the extract comprises:
   (i) from about 1% to about 15% by weight of nuzhenide;
   (ii) from about 1% to about 17% by weight of GL3;
   (iii) from about 0.5% to about 1% by weight of oleoside methyl ester;
   (iv) from about 0.03% to about 0.12% by weight of excelside B;
   (v) from about 0.1% to about 1.7% by weight of GL5; and
   (vi) from about 0.08% to about 0.7% by weight of salidroside.

8. The method according to claim 1, wherein the extract comprises about 10% by weight nuzhenide and about 10% by weight GL3.

9. The method according to claim 1, wherein the extract is a hydro-ethanolic extract.

10. The method according to claim 9, wherein the hydro-ethanolic extract is obtained using a solvent containing from about 30% to about 75% ethanol.

11. The method according to claim 1, wherein the extract is administered in the form of:
    (a) a pharmaceutical composition comprising the *Fraxinus angustifolia* extract and optionally a pharmaceutically acceptable excipient; or
    (b) a food composition comprising the *Fraxinus angustifolia* extract and optionally a food acceptable ingredient.

12. The method according to claim 11, wherein the composition is for oral administration.

13. The method according to claim 1, wherein the method is performed on a human subject.

* * * * *